(12) United States Patent
Webster et al.

(10) Patent No.: US 9,765,233 B2
(45) Date of Patent: Sep. 19, 2017

(54) BIOBASED HIGHLY FUNCTIONAL OLIGOMERS AND THERMOSETS THEREFROM

(71) Applicant: NDSU RESEARCH FOUNDATION, Fargo, ND (US)

(72) Inventors: Dean C. Webster, Fargo, ND (US); Arvin Yu, Fargo, ND (US)

(73) Assignee: NDSU RESEARCH FOUNDATION, Fargo, ND (US)

( * ) Notice: Subject to any disclaimer, the term of this patent is extended or adjusted under 35 U.S.C. 154(b) by 0 days.

(21) Appl. No.: 15/135,144

(22) Filed: Apr. 21, 2016

(65) Prior Publication Data
US 2016/0311754 A1    Oct. 27, 2016

Related U.S. Application Data

(60) Provisional application No. 62/150,591, filed on Apr. 21, 2015, provisional application No. 62/306,858, filed on Mar. 11, 2016.

(51) Int. Cl.
| | |
|---|---|
| *C09D 175/12* | (2006.01) |
| *C08G 59/02* | (2006.01) |
| *C09D 133/10* | (2006.01) |
| *C07C 69/67* | (2006.01) |
| *C09D 133/06* | (2006.01) |
| *C09D 133/08* | (2006.01) |

(52) U.S. Cl.
CPC ............ *C09D 133/10* (2013.01); *C07C 69/67* (2013.01); *C09D 133/06* (2013.01); *C09D 133/08* (2013.01)

(58) Field of Classification Search
CPC ....... C09D 175/12; C08G 59/027; C08K 5/17
See application file for complete search history.

(56) References Cited

U.S. PATENT DOCUMENTS

| 3,248,404 A * | 4/1966 | Werdelmann et al. ............ C07D 301/14 525/333.2 |
|---|---|---|
| 2002/0013396 A1 * | 1/2002 | Benecke ............... C08K 5/0016 524/315 |

OTHER PUBLICATIONS

Adekunle et al., "Synthetic Modification of Reactive Soybean Oils for Use as a Biobased Thermoset Resins in Structural Natural Fiber Composites", Polymer Preprints, 2008, 49(1), pp. 279-280.

Adekunle et al., "Biobased Composites Prepared by Compression Molding with a Novel Thermoset Resin from Soybean Oil and a Natural-Fiber Reinforcement", Journal of Applied Polymer Sci., vol. 116, 2010, pp. 1759-1765.

Adekunle et al., "Synthesis of Reactive Soybean Oils for Use as a Biobased Thermoset Resins in Structural Natural Fiber Composites", Journal of Applied Polymer Sci., vol. 115, 2010, pp. 3137-3145.

Can et al., "Rigid, Thermosetting Liquid Molding Resins From Renewable Resources. I. Synthesis and Polymerization of Soy Oil Monoglyceride Maleates", Journal of Applied Polymer Sci., vol. 81, 2001, pp. 69-77.

Khot et al., "Development and Application of Triglyceride-Based Polymers and Composites", Journal of Applied Polymer Sci., vol. 82, 2001, pp. 703-723.

John La Scala and Richard P. Wool "Property analysis of triglyceride-based thermosets", Polymer 46, 2005, pp. 61-69.

John La Scala and Richard P. Wool "Rhealogy of Chemically Modified Triglycerides", Journal of Applied Polymer Sci., vol. 95, 2005, pp. 774-783.

Lu et al., "New sheet molding compound resins from soybean oil. I. Synthesis and characterization", Polymer 46, 2005, pp. 71-80.

Yongshang Lu and Richard C. Larock "Novel Polymeric Materials from Vegetable Oils and Vinyl Monomers: Preparation, Properties, and Applications", ChemSusChem, 2009, 2, pp. 136-147.

O'Donnell et al., "Natural fiber composites with plant oil-based resin", Composites Sci. and Tech. 64, 2004, pp. 1135-1145.

* cited by examiner

*Primary Examiner* — Robert Harlan
(74) *Attorney, Agent, or Firm* — J.A. Lindeman & Co., PLLC

(57) ABSTRACT

The invention relates to a polyfunctional bio-based oligomer which is the reaction product of a) at least one epoxidized sucrose fatty acid ester resin; b) at least one ethylenically unsaturated acid selected from methacrylic acid, acrylic acid, crotonic acid, and mixtures thereof; c) at least one acid anhydride selected from acetic acid anhydride, acrylic acid anhydride, methacrylic acid anhydride, crotonic acid anhydride, and mixtures thereof; d) optionally, at least one catalyst; and e) optionally, at least one inhibitor. In a polyfunctional bio-based oligomer of the invention, the ratio of ethylenically unsaturated acid to acid anhydride ranges from 90:1 to 1:90; at least one epoxide group of the at least one epoxidized sucrose fatty acid ester resin is esterified by at least one ethylenically unsaturated acid; and at least one epoxide group of the at least one epoxidized sucrose fatty acid ester resin is esterified by at least one acid anhydride. Other embodiments of the invention relate to methods of making the polyfunctional bio-based oligomers of the invention and to curable coating compositions containing them.

14 Claims, 26 Drawing Sheets

US 9,765,233 B2

BIOBASED HIGHLY FUNCTIONAL OLIGOMERS AND THERMOSETS THEREFROM

CROSS-REFERENCE TO RELATED APPLICATIONS

This application claims priority under 35 USC §119 to U.S. Patent Application No. 62/150,591, filed Apr. 21, 2015, and to U.S. Patent Application No. 62/306,858, filed Mar. 11. 2016, which are both incorporated herein by reference.

STATEMENT OF US GOVERNMENT SUPPORT

This invention was made with government support under IIA-1355466 awarded by the National Science Foundation (NSF). The US government has certain rights in the invention.

FIELD OF THE INVENTION

This invention relates to the field of functionalized bio-based resins and curable coating compositions containing bio-based resins. More particularly, this invention relates to novel biobased resins containing a high number of unsaturated ester groups.

BACKGROUND OF THE INVENTION

Thermosetting polymers and composites have been widely used in modern industry because of their low density, good mechanical properties, low cost, dimensional stability, and so on. Important monomers and oligomers for thermosets include unsaturated polyester, epoxy resin, vinyl ester, phenol-formaldehyde resin, melamine resin, etc. Traditionally, most of these resins have been synthesized using petroleum-based chemicals as the raw materials. However, due to the foreseeable limit of fossil feedstocks and the increasing environmental concerns, the polymer and composites industry is suffering from potential increasing cost and environmental regulations. Therefore, much effort has been devoted lately to develop polymers and composites from bio-renewable raw materials. See Wool et al., *Biobased Polymers and Composites*, Elsevier, Amsterdam (2005); Belgacem et al., *Monomers, Polymers, and Composites from Renewable Resources*, Elsevier, Amsterdam (2008); Raquez et al., *Prog. Polym. Sci.* 35:487-509 (2010). The fluctuating price of petroleum-based products and stricter environmental rules and regulations increases the demand for bio-based products. Compared to petroleum-based products, bio-based products are environmentally friendly, sustainable, and versatile in use. See Deka et al., *Progress in Organic Coatings* 66:192-192 (2009). In 2004, the world production from major oils totaled 380 million metric tons. Production has continued to rise at a rate of 3-4% per year with soybean oil the major oil produced. See Behera et al., *Journal of Applied Polymer Science* 109:2583-2590 (2008).

Plant oils are one of the most important bio-renewable chemical feedstocks for the polymer industry because of their high annual production, high availability, low toxicity, relatively low cost, and biodegradability. Plant oils and their derivatives have been widely used for the production of paints and coatings since the development of drying oil resins, taking advantage of the autoxidation crosslinking of the double bonds in the fatty acid chains. See Meier et al., *Chem. Soc. Rev.* 36:1788-1802 (2007); Xia et al., *Green Chem.* 13:1983-1909 (2010). During the last decade, a variety of plant oil-based polymers have been developed via free radical or cationic homo-polymerization, as well as copolymerization with petroleum-based monomers, such as styrene and divinylbenzene. See Lu et al., *ChemSusChem* 2:136-147 (2009); Li et al., *Biomacromolecules* 4:1018-1025 (2003); Kundu et al., *Biomacromolecules* 6:797-806 (2005); Henna et al., *J. Appl. Polym. Sci.* 104:979-985 (2007); Valverde et al., *J. Appl. Polym. Sci.* 107:423-430 (2008); Andjelkovic et al., *Polymer* 46:9674-9685 (2005); Andjelkovic et al., *Biomacromolecules* 7:927-936 (2006); Lu et al., *Biomacromolecules* 7:2692-2700 (2006). Bio-based vegetable oils (e.g., soybean oil) contain triglycerides that are composed of three unsaturated fatty acid chains joined at a glycerol junction. See Fu et al., *Journal of Applied Polymer Science* 117:2220-2225 (2010). However, due to the relatively low reactivity of the double bonds in the fatty acid chain, some chemical modifications are usually needed to introduce reactive functional groups having higher reactivity. A widely explored method for the modification of plant oils involves the conversion of the double bonds to epoxy groups by using peracids and hydrogen peroxides. With the epoxidation, polymerization occurs quickly with highly cross linked networks. See Behera et al., *Journal of Applied Polymer Science* 109:2583-2590 (2008); Kolot et al., *Journal of Applied Polymer Science* 91:3835-3843 (2003). Epoxidized plant oils have been utilized for coatings and composites by using conventional epoxy curing agents, such as amine and anhydride. However, the internal epoxy groups in epoxidized plant oils are much less reactive than the terminal epoxy groups in benchmark materials, for example bisphenol-A epoxy. Therefore, epoxidized plant oils have been further modified via the ring-opening reaction of epoxy with unsaturated acids or alcohols to produce (meth)acrylated plant oils or plant oil-based polyols. These derivatives have been widely used to generate thermosets by free radical cure or hydroxyl-isocyanate reactions. See Wu et al., *Polym. Int.* 60:571-575 (2011); Lu et al., *Polymer* 46:71-80 (2005); La Scala et al., *Polymer* 46:61-69 (2005); Can et al., *J. Appl. Polym. Sci.* 81:69-77 (2001); Pfister et al., *ChemSusChem* 4:703-717 (2011); Desroches et al., *Polym. Rev.* 52:38-79 (2012); Lu et al., *Biomacromolecules* 8:3108-3114 (2007); Lu et al., *ChemSusChem* 3:329-333 (2010); Petrovic, *Polym. Rev.* 48:109-155 (2008). Besides epoxidization, plant oils have also been modified by hydroformylation (see Petrovic et al., *Polym. Int.* 57:275-281 (2008); Petrovic et al., *Eur. J. Lipid Sci. Technol.* 112:97-102 (2010)) and thiol-ene reactions (see Meier et al., *Macromol. Rapid Commun.* 31:1822-1826 (2010); Turunc et al., *Green Chem.* 13:314-320 (2011); Wu et al., *ChemSusChem* 4:1135-1142 (2011)).

Vegetable oils have been modified using maleinization, epoxidation, acrylation, and hydroxomethylation. See Fu et al., *Journal of Applied Polymer Science* 117:2220-2225 (2010). Epoxidation and acrylation are the most common forms of modification of soybean oils with acrylated soybean oils (ASO) being the most prevalent. See Bunker et al., *Journal of Oil and Colour Chemists's Association* 83:460 (2000). Soybean oils have a wide distribution of functional groups, 0-9 polymerizable groups per molecule. Thus, allowing for substances to react readily to them. The double bonds and highly reactive end groups allows for free radical polymerization to occur. See Fu et al., *Journal of Applied Polymer Science* 117:2220-2225 (2010); Behera et al., *Journal of Applied Polymer Science* 109:2583-2590 (2008). Acrylated soybean oils (ASO) are used to form solvent-free curing of films, adhesives, coatings, inks, and varnishes. Acrylation of epoxidized soybean oil, will lead to great improvement of photoactivity because of the short time it takes to form crosslinks under ultraviolet radiation. See Pelletier et al., *Journal of Applied Polymer Science* 99:3218-3221 (2005).

The biggest obstacle in the application of plant oils for the generation of polymers is the flexibility of the fatty acid chain, which leads to low glass transition temperature ($T_g$) and low mechanical properties such as modulus and hardness. Thus, plant oils cannot be used by themselves as structural and engineering materials. To overcome these limitations, petroleum-based monomers (for example styrene) are usually introduced to reinforce plant oil-based polymers, but the bio-renewable content is sacrificed to achieve the desired material properties in this approach. See Li et al., *Biomacromolecules* 4:1018-1025 (2003); Khot et al., *J. Appl. Polym. Sci.* 82:703-723 (2011).

Sucrose is a bio-renewable polyol that is naturally present in a variety of plants. Sucrose ester is a vegetable oil composed of sucrose and fatty acids that is frequently used as a bio-based curable material for decades. See Jinli et al., *Chinese Journal of Chemical Engineering* 17:1033-1037 (2009). The fatty esters of sucrose were first explored as a coating resin in 1960's. See Bobalek et al., *Official Digest* 33:453-468 (1961); Walsh et al., *Div. Org. Coatings Plastic Chem.* 21:125-148 (1961). However, a high degree of substitution of sucrose with fatty acids had not been achieved until an efficient process was developed by Procter & Gamble (P&G) Chemicals in 2002. See U.S. Pat. Nos. 6,995,232; 6,620,952; 6,887,947. In spite of a relatively high degree of substitution (average of 7.7 fatty acid chains per molecule) and moderate molecular weight (around 2,400 g/mol), sucrose esters of fatty acids have low viscosity (300-400 mPa·s) due to their compact architectures. Highly substituted sucrose esters of fatty acids (SEFAs) have been successfully commercialized under the brand Sefose®, and utilized as a diluent in alkyd resins by CCP. Furthermore, SEFAs are a highly tunable platform such that a variety of derivatives and formulations with different properties and application can be developed, since many of the modification approaches for plant oils are applicable to sucrose esters.

Recently, Pan et al. reported the synthesis of a series of thermosets based on SEFAs. Epoxidized sucrose esters of fatty acids (ESEFAs) were prepared via epoxidization, and cured using cyclic anhydrides. See Pan et al., *Green Chem.* 13:965-975 (2011); Pan et al., *Biomacromolecules* 12:2416-2428 (2011); Pan et al., *Macro. Rapid Comm.* 32:1324-1330 (2011). Esterification of sucrose with soybean oil provides sucrose soyate, which is rigid through the sucrose core. Functionality may be achieved via transformations on the double bond of the fatty acid chains. For example, the double bond may be epoxidized to form epoxidized sucrose soyate, which may be represented by the following structure:

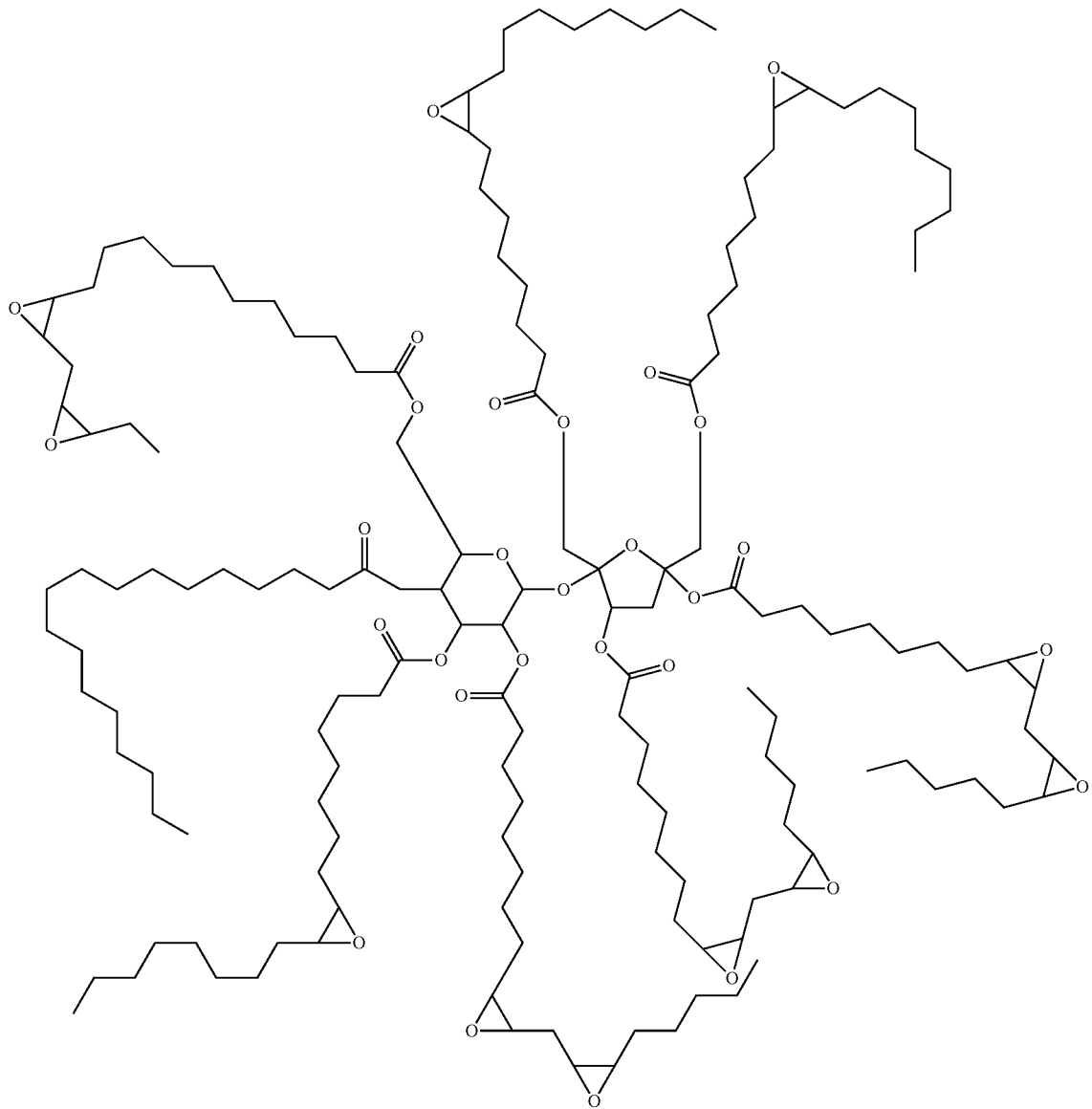 [SMILES: CCCCCCCCCCCCCCCCCC(=O)CC1C(COC(=O)CCCCCCCCCCC2OC2CC2OC2CC)OC(OC2(COC(=O)CCCCCCCC3OC3CCCCCCCC)OC(COC(=O)CCCCCCCC3OC3CCCCCCCC)(OC(=O)CCCCCCCC3OC3CC3OC3CCCCC)CC2OC(=O)CCCCCCCC2OC2CC2OC2CCCCC)C(OC(=O)CCCCCCCC2OC2CC2OC2CCCCC)C1OC(=O)CCCCCCCC1OC1CCCCCCCC]

As described in PCT application PCT/US14/64546, published as WO 2015/070018, which is incorporated herein by reference, a plurality of oxirane groups in epoxidized sucrose soyate can be methacrylated using methacrylic acid. The resins, however, had very high viscosity and styrene diluent was needed to reduce the viscosity.

Even with these developments, there remains a need for additional bio-based resins that expand the number and utility of currently known bio-based resins by introducing improved functionality and functional groups. This invention answers that need.

SUMMARY OF THE INVENTION

This invention relates to novel biobased resins containing a large number of unsaturated ester groups. The resins of the invention are prepared from epoxidized sucrose fatty acid esters, such as those described in published PCT application WO 2011/097484, incorporated herein by reference. The unsaturated ester resins of the invention can be used in various compositions, such as coatings, composites, adhesives, etc.

In one embodiment the invention relates to a polyfunctional bio-based oligomer which is the reaction product of a) at least one epoxidized sucrose fatty acid ester resin; b) at least one ethylenically unsaturated acid selected from methacrylic acid, acrylic acid, crotonic acid, and mixtures thereof; c) at least one acid anhydride selected from acetic acid anhydride, acrylic acid anhydride, methacrylic acid anhydride, crotonic acid anhydride, and mixtures thereof; d) optionally, at least one catalyst; and e) optionally, at least one inhibitor. In the preparation of a polyfunctional bio-based oligomer of the invention, the ratio of ethylenically unsaturated acid to acid anhydride ranges from 90:10 to 1:99; at least one epoxide group of the resulting epoxidized sucrose fatty acid ester resin is esterified by at least one ethylenically unsaturated acid; and at least one epoxide group of the resulting epoxidized sucrose fatty acid ester resin is esterified by at least one acid anhydride.

Other embodiments of the invention relate to methods of making the polyfunctional bio-based oligomers of the invention.

Another embodiment of the invention relates to thermosetting compositions containing a polyfunctional bio-based oligomer of the invention.

BRIEF DESCRIPTION OF THE FIGURES

FIG. 6a) unreacted formulation with 30% styrene and Luperox P and Luperox 10M75, FIG. 6b) cured at 120° C. for 2 h, and FIG. 6c) cured at 120° C. for 2 h and 175° C. for 1 h.

FIG. 13a) DMESS-0.8 (1:9), FIG. 13b) MAcetSS-0.1, and FIG. 13c) MAcetSS-0.3 in Example 5.

FIG. 16a) tensile strength, FIG. 16b) Young's modulus, FIG. 16c) % elongation, and FIG. 16d) toughness.

DESCRIPTION OF THE INVENTION

Figure 1A:
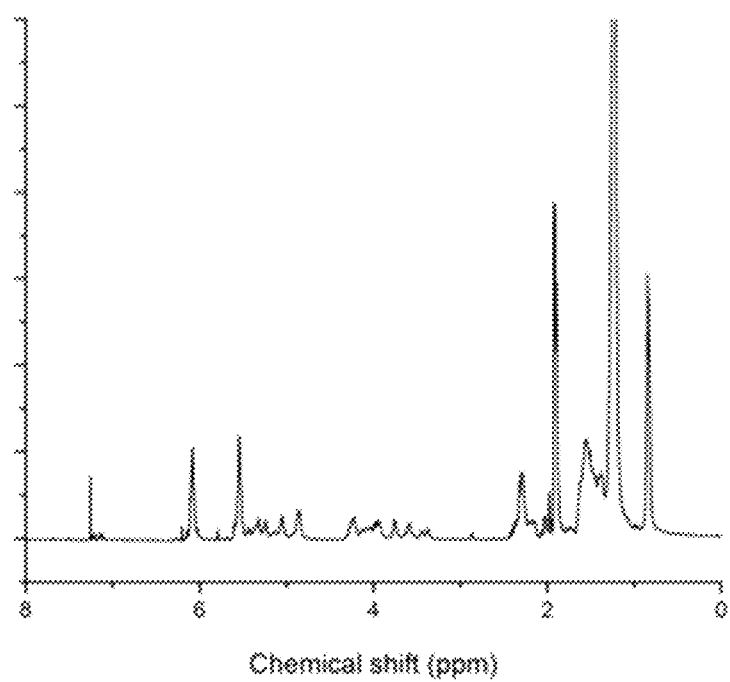
FIG. 1a depicts the full proton NMR spectrum of DMESS and FIG. 1b depicts the expanded view of regions 4.6-6.0 ppm as described in Example 1.

This invention relates to novel biobased resins containing a large number of unsaturated ester groups. The resins of the invention are prepared from epoxidized sucrose fatty acid esters, which are described in published PCT application WO 2011/097484 and Pan et al., Green Chem. 13:965-975 (2011), which are incorporated herein by reference. As described in WO 2011/097484, epoxidized sucrose fatty acid ester resins may be derived from different vegetable oils (coconut oil, corn oil, castor oil, soybean oil, safflower oil, sunflower oil, linseed oil, tall oil fatty acid, tung oil, vernonia oil, etc.) and can be used in the invention. In a preferred embodiment, the epoxidized sucrose ester of soybean oil (epoxidized sucrose soyate (ESS)) is used.

According to the invention, esterifying an epoxidized sucrose fatty acid ester, such as epoxidized sucrose soyate, via its oxirane groups results in a diester at the plurality of oxirane groups in the epoxidized sucrose fatty acid ester. By esterifying the plurality of oxirane groups of the epoxidized sucrose fatty acid ester resin the amount of hydrogen bonding can be reduced, and a lower resin viscosity can be obtained. This can lead to lower amount of styrene diluent being required to achieve a suitable processing viscosity.

One embodiment of the invention relates to a polyfunctional bio-based oligomer which is the reaction product of a) at least one epoxidized sucrose fatty acid ester resin; b) at least one ethylenically unsaturated acid selected from methacrylic acid, acrylic acid, crotonic acid, and mixtures thereof; c) at least one acid anhydride selected from acetic acid anhydride, acrylic acid anhydride, methacrylic acid anhydride, crotonic acid anhydride, and mixtures thereof; d) optionally, at least one catalyst; and e) optionally, at least one inhibitor. In the preparation of a polyfunctional bio-based oligomer of the invention, the ratio of ethylenically unsaturated acid to acid anhydride ranges from 90:10 to 1:99; at least one epoxide group of the resulting epoxidized sucrose fatty acid ester resin is esterified by at least one ethylenically unsaturated acid; and at least one epoxide group of the resulting epoxidized sucrose fatty acid ester resin is esterified by at least one acid anhydride. Other embodiments of the invention relate to methods of making the polyfunctional bio-based oligomers of the invention.

Using, for example, methacrylic acid as the ethylenically unsaturated acid and its corresponding acid anhydride, one possible method involves the synthesis of the esterified epoxidized sucrose fatty acid ester resin from the reaction of methacrylic acid with an epoxidized sucrose fatty acid ester, followed by the reaction with methacrylic anhydride to esterify the hydroxyl group generated by the ring-opening esterification of an oxirane group. For example, the epoxidized sucrose fatty acid ester resin is reacted with a sufficient amount of methacrylic acid to react 80-90% of the epoxide groups in the epoxidized sucrose ester resin. Each reaction generates a hydroxyl group, which is then reacted with methacrylic anhydride to esterify the hydroxyl groups. However, in this procedure, an equivalent amount of methacrylic acid is generated and then needs to be removed from the system, which creates waste and cost.

In one embodiment of the invention, a more efficient process involves the direct double esterification of a plurality of the oxirane groups in the epoxidized sucrose fatty acid ester resin using an ethylenically unsaturated acid, for example, methacrylic acid (A) and methacrylic acid anhydride (B). This may be referred to as dual esterification using an ethylenically unsaturated carboxylic acid and an anhydride (i.e., "dual methacrylation" when methacrylic acid and methacrylic acid anhydride are used). This is shown in Scheme 1, where the epoxidized sucrose fatty acid ester is represented by the $R_1$, $R_2$ oxirane.

Scheme 1.

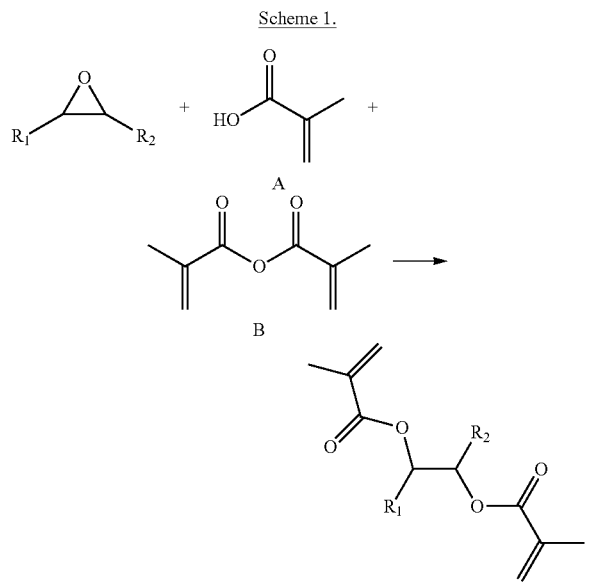

In one embodiment of the invention, the direct double esterification involves the initial addition of an amount of ethylenically unsaturated carboxylic acid to the epoxidized sucrose fatty acid ester resin, followed by the addition of acid anhydride, in a one-pot synthesis. The amount of unsaturated carboxylic acid will generally range from 0.1 to 0.9 equivalents relative to epoxy groups and may be 0.1 to 0.3 equivalents or 0.7 to 0.9 equivalents in other embodiments of the invention. The amount of acid anhydride is generally from 0.1 to 0.9 equivalents relative to epoxy groups and may be 0.1 to 0.3 equivalents or 0.7 to 0.9 equivalents in other embodiments of the invention. The total amount of epoxide groups on the epoxidized sucrose fatty acid ester resin that are reacted with acid plus anhydride may range from 0.1 equivalents to 1.0 equivalents. The molar ratio of ethylenically unsaturated carboxylic acid to acid anhydride generally ranges from 90:10 to 1:99 and may be from 1:9 to 2:8 in other embodiments of the invention. As an example of direct double esterification, a small amount of methacrylic acid is reacted with the oxirane groups of the epoxidized sucrose fatty acid ester resin and then methacrylic anhydride is reacted with the generated hydroxyl groups to esterify some of the hydroxyl groups of the epoxy group, which generates methacrylic acid byproduct. The generated methacrylic acid byproduct then reacts with the remaining plurality of non-methacrylated epoxide groups. Control of the stoichiometry of methacrylic acid and methacrylic anhydride reduces the amount of unreacted methacrylic acid byproduct that needs to be removed. In another embodiment, the epoxy groups of the epoxidized sucrose fatty acid ester resin are directly reacted with methacrylic acid to esterify the epoxy group. In other embodiments, acrylic acid or crotonic acid may be used as the ethylenically unsaturated acid together with their corresponding acid anhydrides. In other embodiments of the invention, mixtures of the acids and anhydrides may be used. In certain embodiments of the invention, methacrylic acid and methacrylic anhydride or acetic acid anhydride are used; acrylic acid and acrylic anhydride or acetic acid anhydride are used or crotonic acid and crotonic anhydride or acetic acid anhydride are used. In another embodiment of the invention, acetic acid anhydride may be used instead of the acid anhydride corresponding to the ethylenically unsaturated acid.

In a sequential or double esterification method of the invention, the epoxidized sucrose fatty acid ester resin is first reacted with the ethylenically unsaturated carboxylic acid to form a first esterified product followed by reacting the first esterified product with the acid anhydride. Scheme 2, below, shows an example of this where the ethylenically unsaturated acid methacrylic acid (A) is first reacted with the epoxidized sucrose fatty acid ester resin represented by the $R_1$, $R_2$ oxirane to form a first esterified product which is then reacted with acetic acid anhydride (B) as the acid anhydride.

Scheme 2

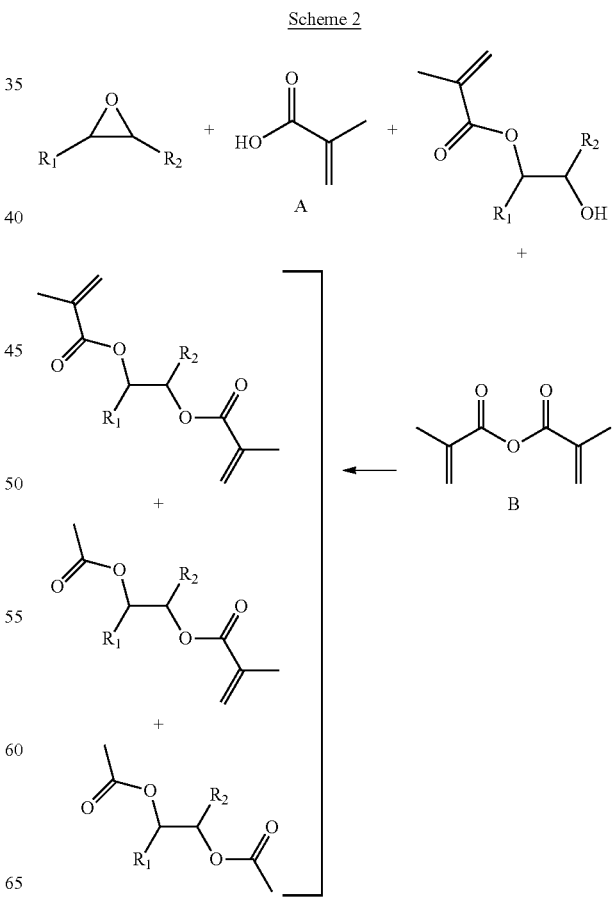

In a sequential or double direct esterification method the reaction initially undergoes epoxide activation by the methacrylic acid. Scheme 3, below, illustrates the overall reaction. Once the methacrylated intermediate (Intermediate A, Scheme 3) is formed, either of the anhydrides may react with the hydroxyl group. The reaction products will be a mixture of dual methacrylated and methacrylate-acetate compounds. After the anhydrides react with the hydroxyl groups, acetic acid and methacrylic acid will be generated in the reaction. These acids will generate both Intermediates A and B. These intermediates will then generate mixtures of dual methacrylated, methacrylate-acetate, and diacetate products.

include, but are not limited to, AMC-2, triphenylphosphine, 1,8-diazabicycloundec-7-ene, K-Pure® CXC-1765, BV Cat 7, and ATC-3. The catalyst may be present in an amount ranging from 0.01 to 2.0 percent of the total weight of the polyfunctional bio-based oligomer. A solvent may be used for an esterification reaction of the invention. Suitable solvents include for example, but are not limited to, toluene, xylenes, methylethyl ketone, acetone, methylamyl ketone, n-butyl acetate, t-butyl acetate, aromatic 100, tetrahydrofuran, and the like.

An inhibitor may be used in the ring-opening reaction between the at least one ethylenically unsaturated acid

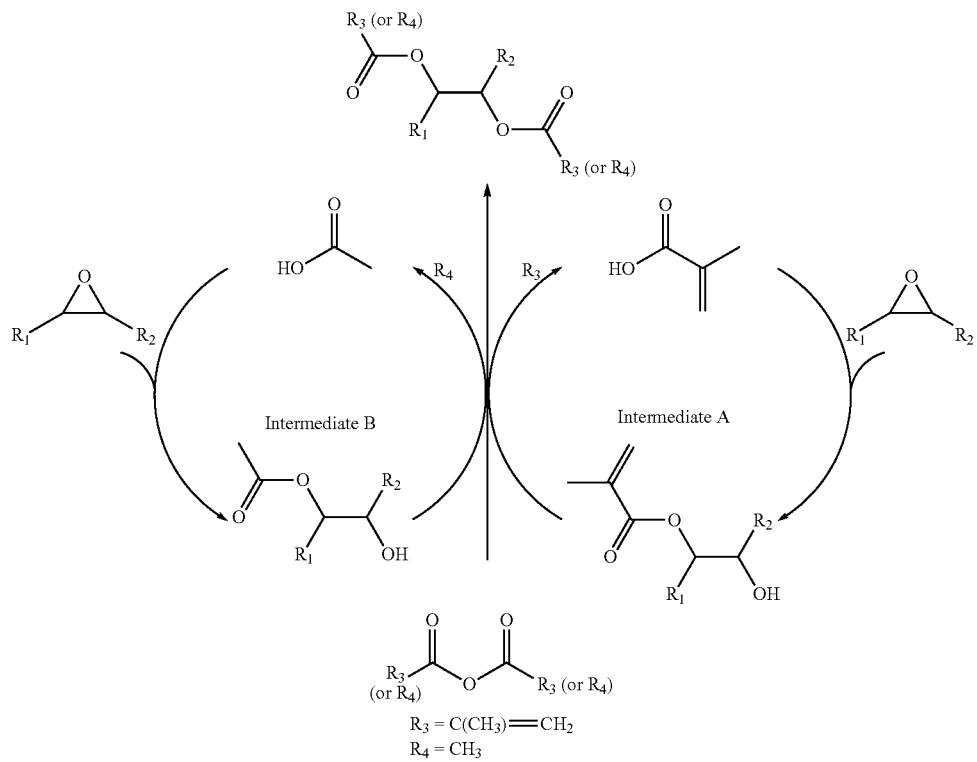

Scheme 3.

$R_3 = C(CH_3)=CH_2$
$R_4 = CH_3$

In one embodiment, the epoxide groups of the polyfunctional bio-based oligomers may be fully esterified, where substantially all of the epoxide groups have been methacrylated, or it may be partially esterified, where only a fraction of the available epoxide groups have been esterified, for example, 25%-90% esterified. In one embodiment, epoxidized sucrose soyate, for example, may be esterified at 25%, 50%, 75%, and 90% esterification. It is understood in the art that some residual epoxide groups may remain even when full esterification is desired. A desired degree of partial esterification may be achieved by using less than the stoichiometric equivalent amount of the total acid component (both the ethylenically unsaturated acid and the acid anhydride) to oxirane groups, while full or substantially full esterification may be achieved by using a stoichiometric equivalent or an excess of the total acid component.

The esterification reactions discussed above generally take place in the presence of a catalyst and an inhibitor. Any catalyst, or inhibitors known in the art may optionally be used facilitate the double esterification of the plurality of oxirane groups. For example, catalysts that may be used selected from methacrylic acid, acrylic acid, and crotonic acid, and the epoxidized sucrose fatty acid ester resin. For example, the inhibitor may be selected from hydroquinone, mono-t-butylhydroquinone, 2,5-di-t-butylhydroquinone, toluhydroquinone, hydroquinone methyl ether, hydroquinone ethyl ether, 4-t-butyl catechol, butylated hydroxyl toluene, and the like, and may be present in an amount ranging from 0.01% to 2.5% of total weight, more preferably 0.1% to 1.0% of the total weight of the polyfunctional bio-based oligomer. A preferred inhibitor that may be used is hydroquinone.

In another embodiment of the invention, different extents of reaction of the epoxy groups can be synthesized as well as different ratios of single esterified epoxy and double esterified epoxy resins.

The polyfunctional bio-based oligomers of the invention can be used in various compositions, such as coatings, composites, adhesives, etc. Initiators that may be used to cure the polyfunctional bio-based oligomers of the invention include, but are not limited to, Luperox-P and Luperox 10M75. The invention also relates to curable coating compositions comprising the polyfunctional bio-based oligomers, which may be formulated with or without solvents. A coating composition may be a solvent-free coating composition or may optionally contain a solvent such as, for example, acetone, THF, methyl ethyl ketone (MEK), xylene, etc. The coating composition may be a solution in such a solvent or mixture of solvents.

In another embodiment, the invention relates to a curable coating composition comprising at least one polyfunctional bio-based oligomer, at least one optional diluent, and at least one optional initiator. The curable coating compositions may be made by mixing at least one polyfunctional bio-based oligomer with at least one optional diluent and at least one optional initiator. In another embodiment, the invention relates to thermoset coatings formed from the curable coating compositions of the invention.

A further embodiment of the invention involves the free radical curing of the polyfunctional bio-based oligomers and coating compositions containing these oligomers. Formulations may be prepared by mixing the oligomer resin with an optional diluent, an optional solvent, and an initiator.

When a coating composition contains a polyfunctional bio-based oligomer, the diluents may be ones used in free radical or vinyl polymerizations such as, but not limited to, styrene, bisphenol A diglycidylether methacrylate (Bis-GMA), ethylene glycol dimethacrylate, 1,4-butanediol dimethacrylate, polyethylene glycol dimethacrylate, trimethylolpropane trimethacrylate, triethyleneglycol dimethacrylate (TEGDMA), isodecyl acrylate, 2-hydroxyethyl acrylate, butyl acrylate, 2-ethylhexyl acrylate, 1,6-hexanediol diacrylate, trimethylolpropane triacrylate, pentaerythritol tetraacrylate, ethoxylated trimethylolpropane triacrylate, and acrylated epoxidized soybean oil.

For photoccuring of the polyfunctional bio-based oligomers and coating compositions containing these oligomers, a free radical photoinitiator is needed. Suitable free radical photoinitiators include cleavage or Norrish I type photoinitiators or Norrish type II photoinitiators known in the art. Examples of Norrish type I photoinitiators are 2-hydroxy-2-methyl-1-phenyl-1-propanone, 2,2-diethoxyacetophenone, benzildimethylketal, 1-hydroxycyclohexylphenyl-ketone, 2,2'dimethoxy-2-phenylacetophenone, and the like. Examples of Norrish type II photoinitiators are benzophenone, benzio, xanthone, thioxanthone, and the like, combined with synergists such as triethanolamine, triethylamine, dimethylethanol amine, and the like.

For thermal curing, a thermally initiated free radical initiator is needed. Suitable thermally initiated free radical initiators include dialkyl peroxides, such as, for example, dicumyl peroxide, di-t-butyl peroxide, di-t-amyl peroxide, alpha, alpha' di(t-butyl peroxy diisopropyl benzenes, 2,5-dimethyl-2,5-di-(t-butyl peroxy) hexane, 2,5-dimethyl-2,5-di-(t-butyl peroxy) hexyne-3, t-butyl cumyl peroxide; diacyl peroxides, such as, for example, dibenzoyl peroxide, succinic acid peroxide, dilauryl peroxide, didecanoyl peroxide; diperoxyketals, such as, for example, 1,1-di(t-butylperoxy)-3,3,5-trimethylcyclohexane, 1,1-di(t-butylperoxy)-cyclohexane, 1,1-di(t-amylperoxy)cyclohexane, n-butyl-4,4-di(t-butylperoxy)valerate, ethyl-3,3-di(t-amylperoxy)butyrate, ethyl-3,3-di(t-butylperoxy) butyrate; hydroperoxides, such as, for example, cumene hydroperoxide, diisopropylbenzene hydroperoxide, t-butyl hydroperoxide, t-amyl hydroperoxide; ketone peroxides, such as, for example, methyl ethyl ketone peroxide, 2,4-pentanedione peroxide; peroxydicarbonates, such as, for example, di(n-propyl) peroxydicarbonate, di(sec-butyl) peroxydicarbonate, di(2-ethylhexyl) peroxydicarbonate; peroxyesters, such as, for example, alpha-cumyl peroxy neodecanoate, t-amyl peroxy neodecanoate, t-butyl peroxy neodecanoate, t-amyl peroxypivalate, t-butyl peroxypivalate, 2,5-di(2-ethylhexanoylperoxy) 2,5-dimethylhexane, t-amyl peroxy 2-ethylhexanoate, t-butyl peroxy-2-ethylhexanoate, t-amyl peroxyacetate, t-butyl peroxyacetate, t-butyl peroxybenzoate, OO-(t-amyl) O-(2-ethylhexyl) monoperoxycarbonate, OO-(t-butyl) O-isopropyl monoperoxycarbonate, OO-(t-butyl) O-(2-ethylhexyl) monoperoxycarbonate, poly-t-butylperoxy carbonate; azo initiators, such, for example, as 2,2'-azobis(2,4-dimethyl-pentanenitrile), 2,2'-azobis-(2-isobutyronitrile), 2,2'-azobis(2-methylbutyronitrile), 1,1'-azodicyclohexanecarbonitrile; and the like. Mixtures of initiators can be used.

When a composition containing a polyfunctional bio-based oligomer is thermally cured, the composition may further comprise a diluent selected from, for example, styrene, bisphenol A diglycidylether methacrylate (Bis-GMA), triethyleneglycol dimethacrylate (TEGDMA), isodecyl acrylate, isodecyl methacrylate, 2-hydroxyethyl acrylate, 2-hydroxyethyl methacrylate, butyl acrylate, butyl methacrylate, 2-ethylhexyl acrylate, 2-ethylhexyl methacrylate, 1,6-hexanediol diacrylate, 1,6-hexanediol dimethacrylate, trimethylolpropane triacrylate, trimethylolpropane trimethacrylate, pentaerythritol tetraacrylate, pentaerythritol tetramethacrylate, ethoxylated trimethylolpropane triacrylate, ethoxylated trimethylolpropane trimethacrylate, acrylated epoxidized linseed oil, methacrylated epoxidized linseed oil, acrylated epoxidized soybean oil, and methacrylated epoxidized soybean oil.

The invention also relates to the use of a coating composition comprising the polyfunctional bio-based oligomers of the invention, which may be coated onto a substrate and cured using techniques known in the art. The substrate can be any common substrate such as paper, polyester films such as polyethylene and polypropylene, metals such as aluminum and steel, glass, urethane elastomers, primed (painted) substrates, and the like. The substrate may also be dental restorative materials. The coating composition of the invention may be cured thermally or photochemically, e.g., UV or electron beam cure. In another embodiment, the invention relates to an article of manufacture comprising a thermoset coating composition of the invention, such as, for example, dental resin composites.

The invention also relates to the use of a composition comprising the polyfunctional bio-based oligomers of the invention, together with the optional initiators, diluents, catalysts, inhibitors, pigments, and solvents discussed herein, as a matrix resin for composites. For example, the composites may contain at least one layer of fibrous reinforcement material including, for example, those that add to the strength or stiffness of a composite when incorporated with the polyfunctional bio-based methacrylated oligomers of the invention. Non-limiting examples of reinforcing materials can be in the form of filaments, fibers, rovings, mats, weaves, fabrics, knitted material, cloth, PVC, PAN, PET, balsa, paper honeycomb, PP honeycomb of composite reinforcement, glass, Kevlar®, Spectra®, graphite, basalt, boron, or other known structures. Suitable reinforcement materials include glass fibers and fabrics, carbon fibers and fabrics, aramid fibers and fabrics, polyolefin fibers or fabrics (including ultrahigh molecular weight polyethylene fabrics such as those produced by Honeywell under the Spectra trade name), and polyoxazole fibers or fabrics (such as those produced by the Toyobo Corporation under the Zylon trade name). Other examples of reinforcement materials include core materials, such as, for example, various polymer foams, Nida-Core DIAB PVC, Gurit Corecell®, Airex® PVC and PET, Armacell® PET, ProBalsa® balsa, and BALTEK® balsa.

A curable coating composition according to the invention may also comprise a pigment (organic or inorganic) and/or other additives and fillers known in the art. For example, a coating composition of the invention may further contain coating additives. Such coating additives include, but are not limited to, one or more leveling, rheology, and flow control agents such as silicones, fluorocarbons or cellulosics; extenders; reactive coalescing aids such as those described in U.S. Pat. No. 5,349,026, incorporated herein by reference; plasticizers; flatting agents; pigment wetting and dispersing agents and surfactants; ultraviolet (UV) absorbers; UV light stabilizers; tinting pigments; colorants; defoaming and antifoaming agents; anti-settling, anti-sag and bodying agents; anti-skinning agents; anti-flooding and anti-floating agents; biocides, fungicides and mildewcides; corrosion inhibitors; thickening agents; or coalescing agents. Specific examples of such additives can be found in Raw Materials Index, published by the National Paint & Coatings Association, 1500 Rhode Island Avenue, N.W., Washington, D.C. 20005. Further examples of such additives may be found in U.S. Pat. No. 5,371,148, incorporated herein by reference.

Examples of flatting agents include, but are not limited to, synthetic silica, available from the Davison Chemical Division of W. R. Grace & Company as SYLOID®; polypropylene, available from Hercules Inc., as HERCOFLAT®; synthetic silicate, available from J. M. Huber Corporation, as ZEOLEX®.

Examples of viscosity, suspension, and flow control agents include, but are not limited to, polyaminoamide phosphate, high molecular weight carboxylic acid salts of polyamine amides, and alkylene amine salts of an unsaturated fatty acid, all available from BYK Chemie U.S.A. as ANTI TERRA®. Further examples include, but are not limited to, polysiloxane copolymers, polyacrylate solution, cellulose esters, hydroxyethyl cellulose, hydroxypropyl cellulose, polyamide wax, polyolefin wax, hydroxypropyl methyl cellulose, polyethylene oxide, and the like.

Solvents may also be added to the curable coating compositions in order to reduce the viscosity. Hydrocarbon, ester, ketone, ether, ether-ester, alcohol, or ether-alcohol type solvents may be used individually or in mixtures. Examples of solvents can include, but are not limited to benzene, toluene, xylene, aromatic 100, aromatic 150, acetone, methylethyl ketone, methyl amyl ketone, butyl acetate, t-butyl acetate, tetrahydrofuran, diethyl ether, ethylethoxy propionate, isopropanol, butanol, butoxyethanol, and so on.

EXAMPLES

Methods: The following methods are used in the examples for the characterization of the compounds synthesized and materials prepared.

Proton nuclear magnetic resonance spectroscopy ($^1$H-NMR) was conducted with a Bruker system, Ascend 400 MHz magnet with an Avance III HD console (Bruker BioSpin Corporation, Billerica, Mass., USA), using $CDCl_3$ as the solvent.

Fourier transform infrared spectroscopy (FTIR) was performed with a Thermo Scientific Nicolet 8700 with a detector type of DTGS KBr under nitrogen purge. Diluted thin films of the samples were applied on a KBr plate and the absorption spectra were taken with 32 scans at a resolution of 4 $cm^{-1}$.

The thermal stability of the thermosets was determined using a Q500 thermogravimetric analysis (TGA) system (TA Instruments) with a heating rate of 20° C./min from room temperature to 600° C. under a continuous nitrogen flow.

Molecular weight of the resin was obtained using a gel permeation chromatography (GPC) system (EcoSEC HLC-8320GPC, Tosoh Bioscience, Japan) with a differential refractometer (DRI) detector. Separations were performed using two TSKgel SuperH3000 6.00 mm ID×15 cm columns. The columns and detectors were set at 40° C. Tetrahydrofuran (THF) was used as the eluent with a flow rate of 0.35 ml $min^{-1}$. Samples were prepared at nominally 1 mg $ml^{-1}$ in an aliquot of the eluent and allowed to dissolve at ambient temperature for several hours and the injection volume was 20 µL for each sample. Calibration was conducted using polystyrene standards (Agilent EasiVial PS-H 4 ml).

The glass transition temperature ($T_g$) was determined using a Q800DMA (TA Instruments) operating at 1 Hz and a heating rate of 5° C./min from −50° C. to 200° C. (dual cantilever mode). The tan δ peak was identified as the $T_g$. The storage modulus (E') in the rubbery plateau region was determined at 60° C. above the $T_g$ and used to calculate the crosslink density ($v_e$).

The gel content of the thermosets was determined in order to determine the extent of polymerization. This was done via solvent extraction using dichloromethane. A 500-mL flask containing 300 mL dichloromethane and boiling stones was equipped with a Soxhlet extractor, connected to a condenser. 1 g of the samples were weighed and placed inside the thimble, and extracted for 24 h by dichloromethane. The samples were then dried in vacuum and weighed.

Tensile properties were measured using an Instron 5542 system (Instron Corp., Norwood, Mass., USA) and ASTM D638 dumbbell type V specimens were used with a strain rate of 0.2%/s. Specimen thicknesses were around 1.0 mm.

The bulk viscosities of samples were measured using an ARES rheometer.

Acid value is measured according to ASTM D 465.

Example 1—One-Pot Synthesis of DMESS

Epoxidized sucrose soyate was directly double methacrylated at 90° C. in a one-pot synthesis using methacrylic acid (A), methacrylic anhydride (B), 1% AMC-2, and 0.1% hydroquinone. See Reaction 1 where the epoxidized sucrose soyate with its epoxide groups is represented by the $R_1$, $R_2$ oxirane structure.

Reaction 1

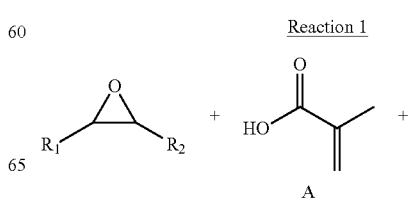

A

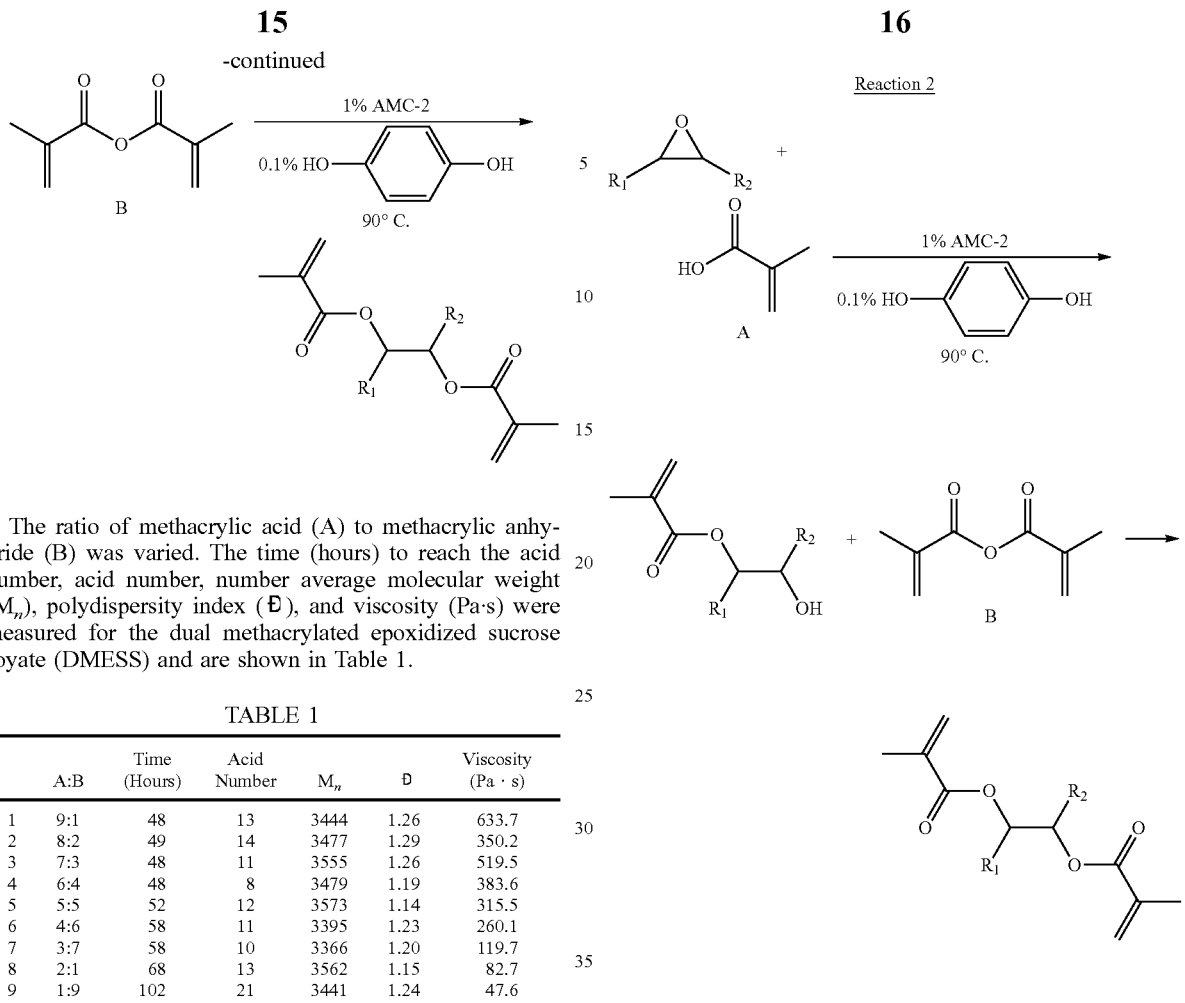

The ratio of methacrylic acid (A) to methacrylic anhydride (B) was varied. The time (hours) to reach the acid number, acid number, number average molecular weight ($M_n$), polydispersity index (Đ), and viscosity (Pa·s) were measured for the dual methacrylated epoxidized sucrose soyate (DMESS) and are shown in Table 1.

TABLE 1

|   | A:B | Time (Hours) | Acid Number | $M_n$ | Đ | Viscosity (Pa · s) |
|---|-----|--------------|-------------|-------|-----|--------------------|
| 1 | 9:1 | 48 | 13 | 3444 | 1.26 | 633.7 |
| 2 | 8:2 | 49 | 14 | 3477 | 1.29 | 350.2 |
| 3 | 7:3 | 48 | 11 | 3555 | 1.26 | 519.5 |
| 4 | 6:4 | 48 | 8  | 3479 | 1.19 | 383.6 |
| 5 | 5:5 | 52 | 12 | 3573 | 1.14 | 315.5 |
| 6 | 4:6 | 58 | 11 | 3395 | 1.23 | 260.1 |
| 7 | 3:7 | 58 | 10 | 3366 | 1.20 | 119.7 |
| 8 | 2:1 | 68 | 13 | 3562 | 1.15 | 82.7 |
| 9 | 1:9 | 102 | 21 | 3441 | 1.24 | 47.6 |

Figure 1B:
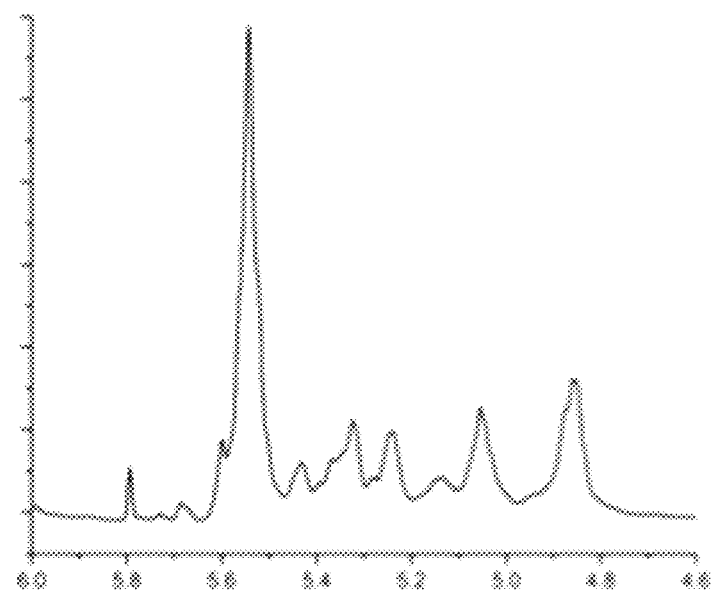
Figure 2:
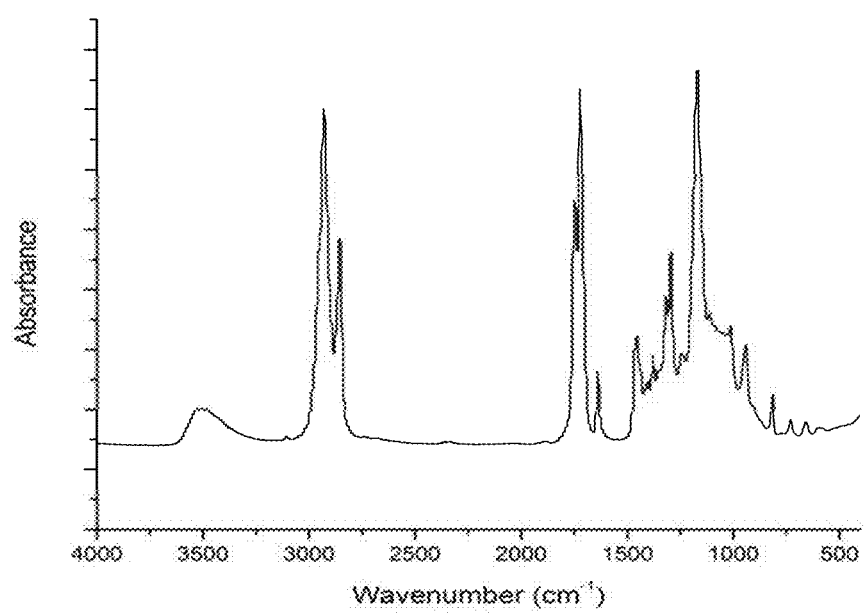
FIG. 2 depicts the FTIR spectrum of DMESS as described in Example 1.

The methacrylated functional group of the epoxidized sucrose soyate was characterized by $^1$H-NMR and FTIR analyses. FIG. 1a depicts the full proton NMR spectrum of DMESS and FIG. 1b depicts the expanded view of regions 4.6-6.0 ppm. FIG. 2 depicts the FTIR spectrum of DMESS. Table 2 lists FTIR wavenumbers of DMESS and their corresponding vibrations.

TABLE 2

| Wavenumber (cm$^{-1}$) | Vibration type |
|---|---|
| 3511 | OH stretching |
| 1750 | Fatty acid C=O stretching |
| 1720 | Methacrylate C=O stretching |
| 1635 | Methacrylate C=C stretching |
| 941  | Epoxide C—O—C deformation bands |
| 812  |  |
| 654  | Methacrylate =C—H out of plane bending |

Example 2—Sequential Addition of Methacrylic Acid and Methacrylic Acid Anhydride Epoxidized sucrose soyate was double methacrylated by the sequential addition of methacrylic acid (A), 1% AMC-2, and 0.1% hydroquinone at 90° C., and then the subsequent addition of methacrylic acid anhydride (B). See Reaction 2 where the epoxidized sucrose soyate with its epoxide groups is represented by the $R_1$, $R_2$ oxirane structure.

The ratio of methacrylic acid (A) to methacrylic anhydride (B), as well as the addition time in both steps, were varied. The acid number after both steps, as well as the viscosity (Pa·s) and time (hours) to reach the acid number of the DMESS, were measured and are shown in Table 3.

TABLE 3

|   | A:B | A Addition Time (Hours) | Acid Number 1 | B Addition Time (Hours) | Acid Number 2 | Viscosity (Pa · s) | Time (Hours) |
|---|-----|-----|-----|-----|-----|-----|-----|
| 1 | 8:2 | 1 | — | 0.33 | 48 | 137.8 | 65 |
| 2 | 8:2 | 23 | 4 | 0.17 | 13 | 263.1 | 46 |
| 3$^a$ | 8:7 | 7.5 | 37 | dropwise | 63 | 30 | 50 |
| 4 | 8:10 | 22 | 1 | dropwise | 85 | 6 | 96 |

$^a$N-Methylimidazole used as second methacrylation catalyst.

Example 3—Catalyst Screening and Sequential Addition

The commercially available catalysts 1,8-diazabicycloundec-7-ene, K-Pure® CXC-1765, BV Cat 7, and ATC-3 were investigated. Table 4 describes the reaction parameters used and the results in terms of the time (hours) to reach the acid number, acid number, number average molecular weight ($M_n$), polydispersity index (Đ), and the viscosity (Pa·s) of the DMESS. It was determined that ATC-3 would be used for the sequential addition of methacrylic acid (A) to epoxidized sucrose soyate and 1% AMC-2 and 0.1% hydroquinone followed by the addition of methacrylic anhydride (B).

TABLE 4

Catalyst screening of the DMESS synthesis.

| A:B | Time (Hours) | Acid Number | Catalyst | Amount (% wt) | $M_n$ | Đ | Comments |
|---|---|---|---|---|---|---|---|
| 1 | 9:1 | 11 | — | DBU | 2 | | | Gelled |
| 2 | 1:1 | 10 | 17 | | 2 | 2204 | 1.17 | Partially gelled |
| 3 | 1:9 | 13 | 13 | | 2 | 1910 | 12.9 | Dark solution |
| 4 | 9:1 | 11 | 36 | K-Pure ® CXC-1765 | 2 | | | Gelled (18 h) |
| 5 | 1:1 | 14 | — | | 2 | | | Gelled |
| 6 | 9:1 | 10 | 52 | | 2 | | | 1% Hydroquinone |
| 7 | 9:1 | 20 | 18 | BV Cat 7 | 1 | | | Dark solution |
| 8 | 9:1 | 12 | 13 | ATC-3 | 1 | 3602 | 1.00 | |

The temperature was varied, while the ratio of methacrylic acid (A):methacrylic anhydride (B) was kept constant. The time (hours) to reach the acid number, acid number, number average molecular weight ($M_n$), polydispersity index (Đ), and the viscosity (Pa·s) of the DMESS were measured and are shown in Table 5.

TABLE 5

Temperature study of the DMESS synthesis.

| A:B | Time (Hours) | Acid Number | Temperature (° C.) | $M_n$ | Đ | Viscosity (Pa·s) | Comments |
|---|---|---|---|---|---|---|---|
| $1^a$ | 1:9 | 53 | 20 | 90 | 3986 | 1.01 | 62.6 | |
| $2^a$ | | 47.5 | 7 | 100 | 3905 | 1.01 | 67.3 | |
| $3^a$ | | 18 | — | 110 | | | | Gelled |
| $4^b$ | | 52 | 9 | 100 | 4140 | 1.01 | 197.6 | |

$^a$80% Methacrylation,
$^b$90% Methacrylation

Example 4

Example 4.1 Resin Synthesis

Figure 3:
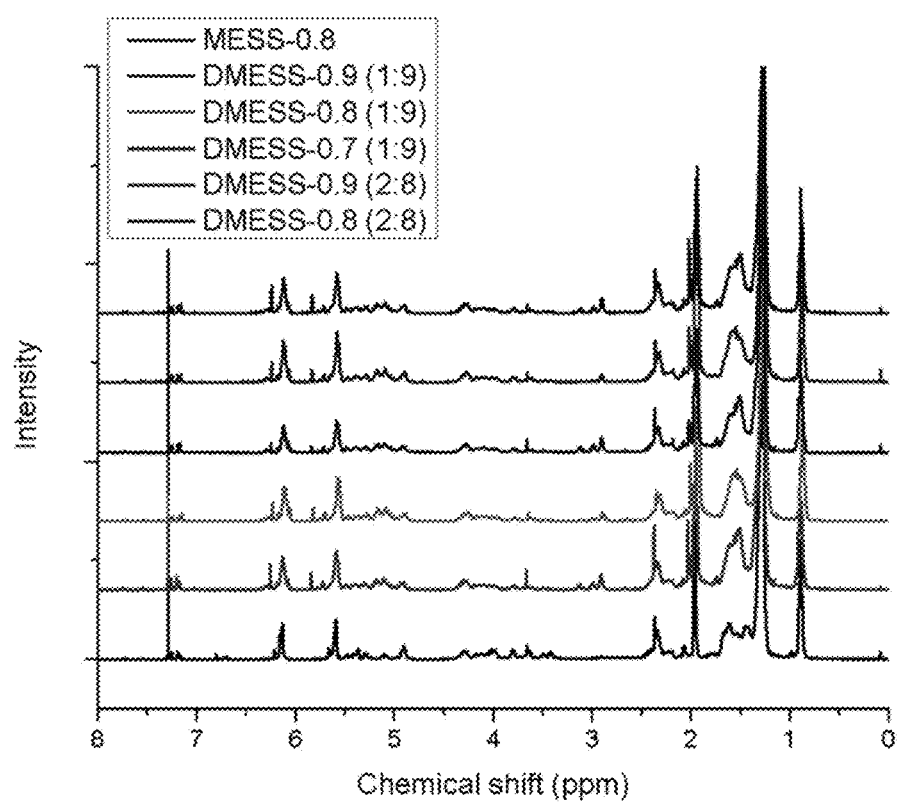
FIG. 3 depicts the $^1$H-NMR spectra of the resins described in Example 4.
Figure 4:
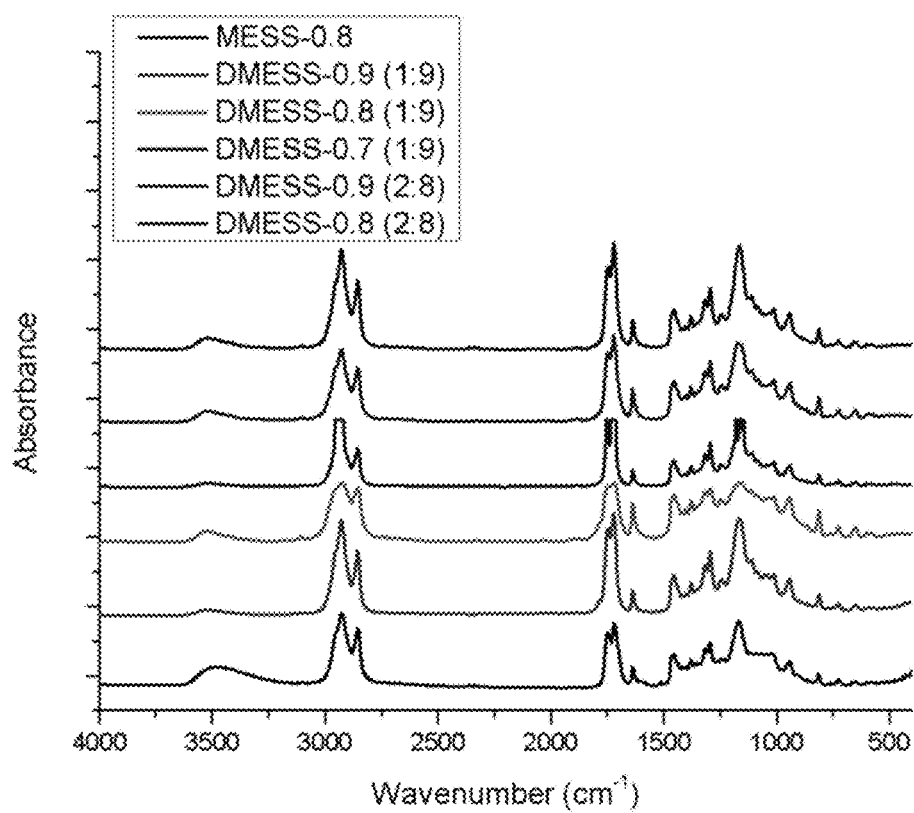
FIG. 4 depicts the FTIR spectra of the resins described in Example 4.

The synthesis of the resin was achieved via ring-opening reaction of ESS with methacrylic acid followed by methacrylic anhydride addition. The reaction was carried out at 100° C., using ATC-3 (1.0% of total weight) as the catalyst and hydroquinone (0.1% of total weight) as the inhibitor. The degree of methacrylation was varied (90%, 80%, and 70%). The molar ratio of methacrylating agents (methacrylic acid and methacrylic anhydride) to epoxy were also varied. The acid to anhydride ratio used were 1:9 and 2:8. A typical procedure to synthesize DMESS-0.8 (line 2 in Table 6 below) is as follows: ESS (100.00 g), methacrylic acid (2.80 g), hydroquinone (0.15 g), and ATC-3 (1.48 g) were placed into a four-necked reaction kettle equipped with a mechanical stirrer and a thermocouple. The mixture was heated at 100° C. until the most of the acid has reacted. Methacrylic anhydride (45.12 g) was added dropwise (~0.25 mL/minute). The reaction mixture was heated at 100° C. until the acid number was less than 15. The final resin appeared as a dark green, viscous liquid. A summary of the amounts used for the synthesis of the DMESS resins is shown in Table 6 and of the properties of the resins produced is shown in Table 7. For comparison MESS-0.8 is the singly methacrylated epoxidized sucrose soyate resin MAESS-0.8 as described in WO 2015/070018. FIG. 3 depicts the $^1$H-NMR spectra of these resins. FIG. 4 depicts the FTIR spectra of these resins. These resins were used in Examples described below.

TABLE 6

Amounts of the reagents used for the synthesis of the various DMESS resins.

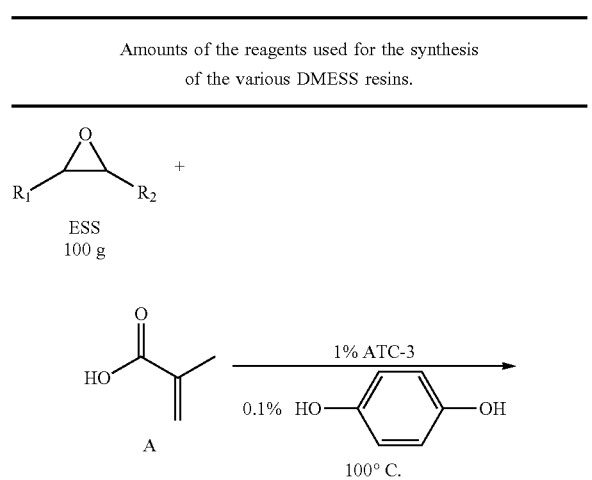

TABLE 6-continued

Amounts of the reagents used for the synthesis of the various DMESS resins.

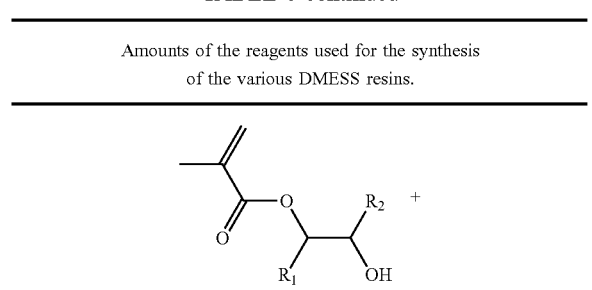

| Resin | Degree of methacrylation (%) | A:B | Methacrylic acid (g) [A] | Methacrylic anhydride (g) [B] |
|---|---|---|---|---|
| DMESS-0.9 | 90 | 1:9 | 3.15 | 50.76 |
| DMESS-0.8 | 80 | 1:9 | 2.80 | 45.12 |
| DMESS-0.7 | 70 | 1:9 | 2.45 | 39.48 |
| DMESS-0.9 | 90 | 2:8 | 6.30 | 45.12 |
| DMESS-0.8 | 80 | 2:8 | 5.60 | 40.11 |

TABLE 7

Properties of the resins.

| Resin | A:B | Temperature (° C.) | Time (Hours) | Acid Number | % Solids | Viscosity (Pa · s) | $M_n$ | Đ |
|---|---|---|---|---|---|---|---|---|
| MESS-0.8 |  | 90 | 23 | 15 | 98.97 | 433.6 | 3748 | 1.01 |
| DMESS-0.9 | 1:9 | 100 | 52 | 9 | 99.85 | 197.6 | 4140 | 1.01 |
| DMESS-0.8 | 1:9 | 100 | 47.5 | 7 | 99.20 | 67.3 | 3905 | 1.01 |
| DMESS-0.7 | 1:9 | 100 | 42 | 6 | 99.98 | 73.2 | 4014 | 1.01 |
| DMESS-0.9 | 2:8 | 100 | 47 | 7 | 99.81 | 198.0 | 4142 | 1.01 |
| DMESS-0.8 | 2:8 | 100 | 51 | 10 | 99.83 | 89.8 | 3976 | 1.01 |

Example 4.2—Viscosities with Styrene

Figure 5:
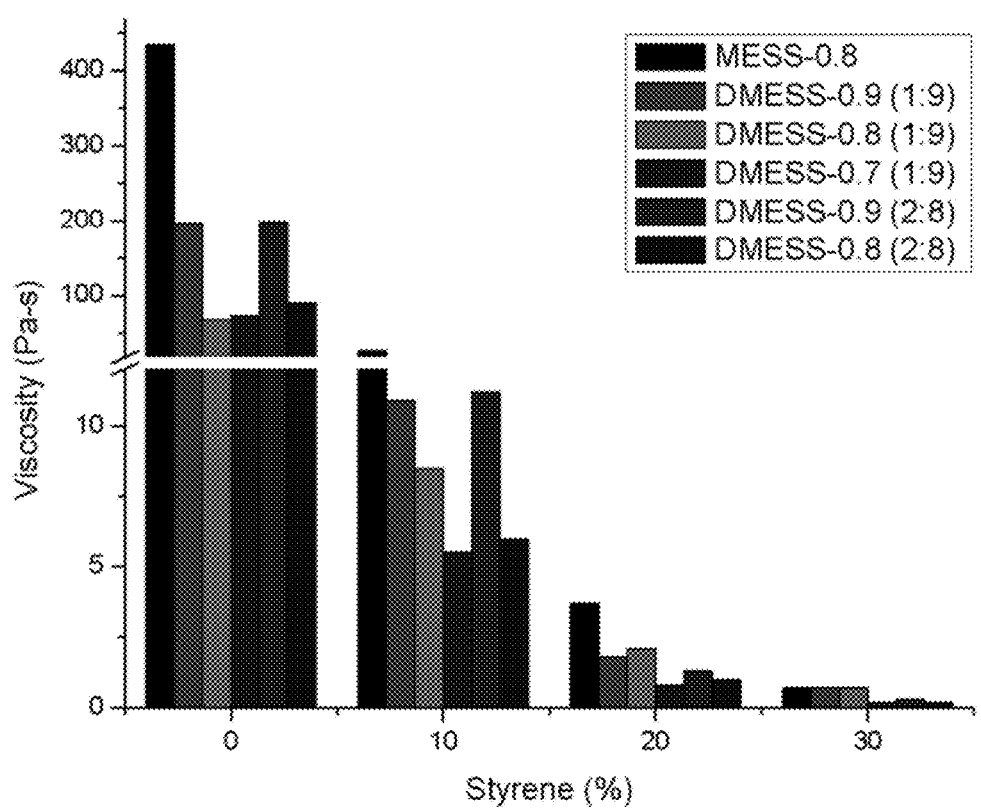
FIG. 5 shows the viscosity of the resins described in Example 4 as a function of styrene content.
Figure 6A:
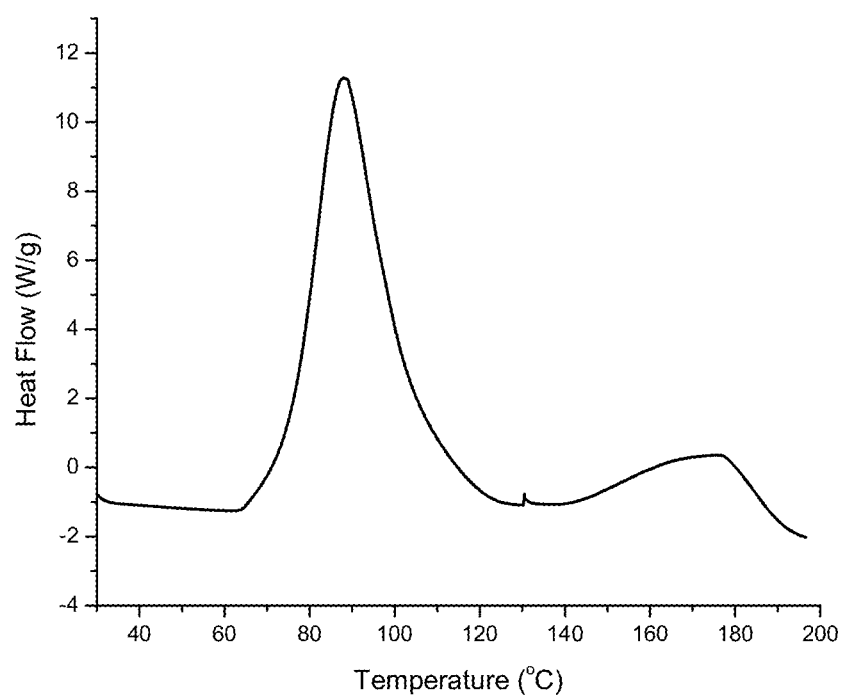
FIGS. 6a, 6b, and 6c show the DSC analyses of DMESS-0.8 (1:9) resin.
Figure 6B:
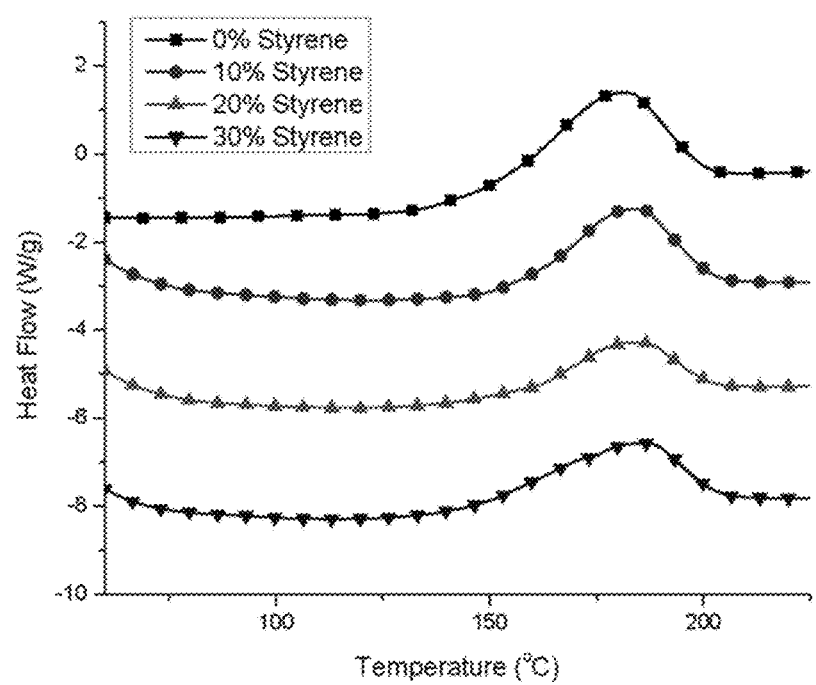
Figure 6C:
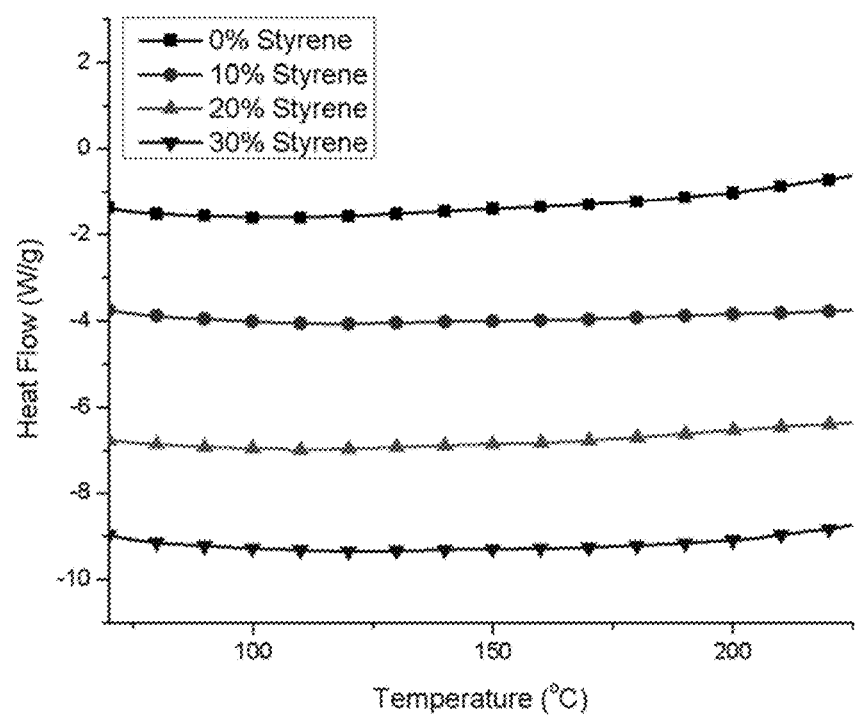
Figure 7A:
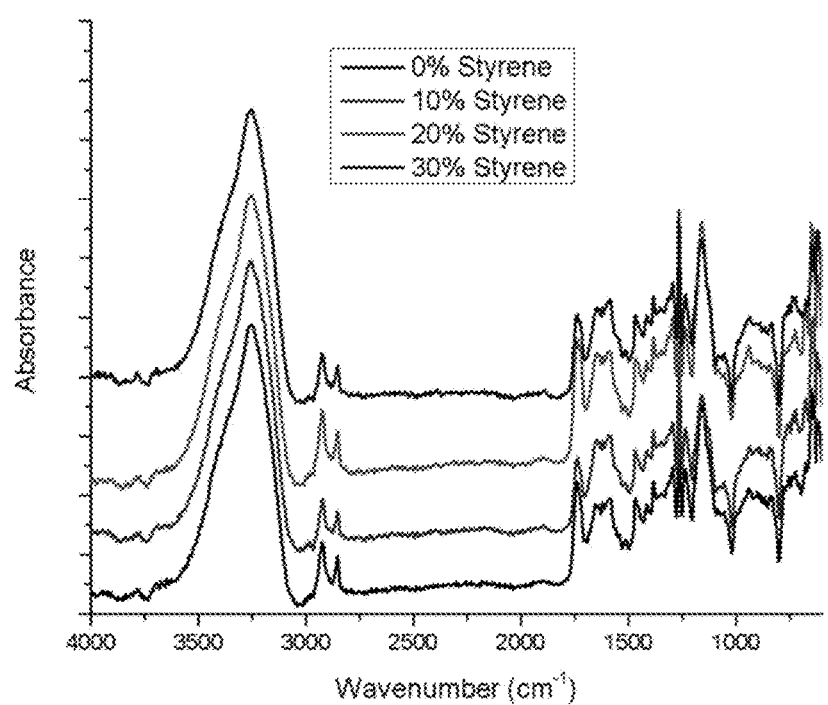
FIGS. 7a and 7b depict the FTIR spectra of DMESS-0.8 (1:9) thermosets cured at: 70° C. for 1 h, 90° C. for 1 h, 120° C. for 1 h (FIG. 7a) and 70° C. for 1 h, 90° C. for 1 h, 150° C. for 2 h (FIG. 7b).
Figure 7B:
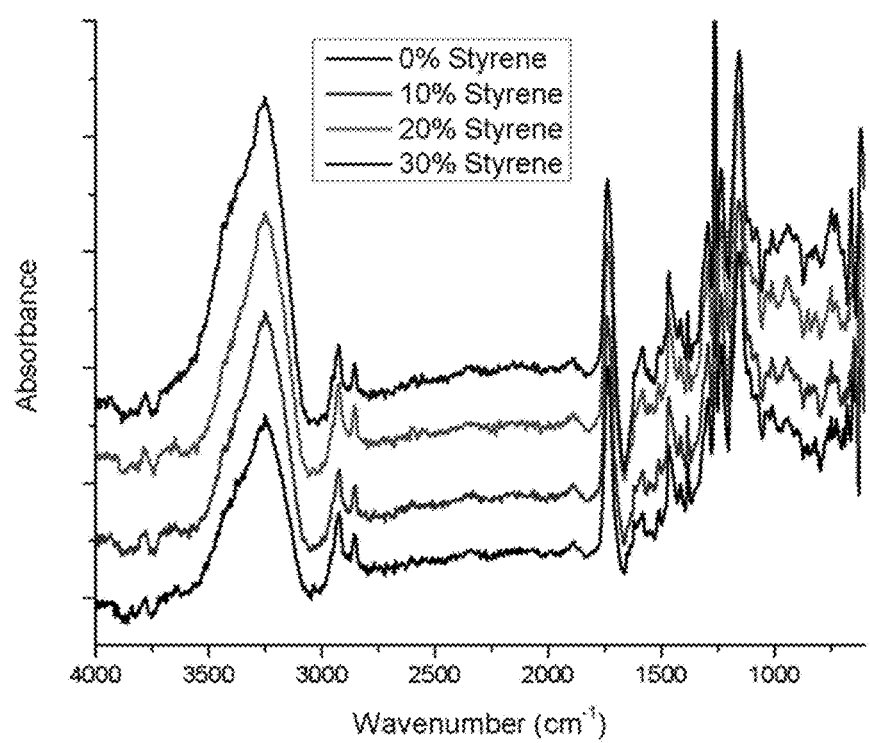

The viscosities of the resins with styrene diluent were measured after the sequential addition of methacrylic acid (A) to epoxidized sucrose soyate followed by the addition of methacrylic anhydride (B). The viscosity (Pa·s) of the MESS-0.8, DMESS-0.7, DMESS-0.8 and DMESS-0.9 (the 0.8 and 0.9 numbers indicate the fraction of epoxy groups on the epoxidized sucrose soyate that are reacted) were measured at varying percentages of styrene diluent and are shown in Table 8. FIG. 5 shows the viscosity of the resins as a function of styrene content. FIG. 6 shows the DSC analyses of DMESS-0.8 (1:9) resin: FIG. 6a) unreacted formulation with 30% styrene and Luperox P and Luperox 10M75, FIG. 6b) cured at 120° C. for 2 h, and FIG. 6c) cured at 120° C. for 2 h and 175° C. for 1 h. FIG. 7 depicts the FTIR spectra of DMESS-0.8 (1:9) thermosets cured at: 70° C. for 1 h, 90° C. for 1 h, 120° C. for 1 h (FIG. 7a) and 70° C. for 1 h, 90° C. for 1 h, 150° C. for 2 h (FIG. 7b).

TABLE 8

Viscosities of the resins with various amounts of styrene.

| Resin | A:B | 0% styrene | 10% styrene | 20% styrene | 30% styrene |
|---|---|---|---|---|---|
| MESS-0.8 |  | 433.6 | 27.2 | 3.7 | 0.7 |
| DMESS-0.9 | 1:9 | 197.6 | 10.9 | 1.8 | 0.7 |
| DMESS-0.8 | 1:9 | 67.3 | 8.5 | 2.1 | 0.7 |
| DMESS-0.7 | 1:9 | 73.2 | 5.5 | 0.8 | 0.7 |
| DMESS-0.9 | 2:8 | 198.0 | 11.2 | 1.3 | 0.3 |
| DMESS-0.8 | 2:8 | 89.8 | 6.0 | 1.0 | 0.2 |

Example 4.3—Thermosets and Thermal Stability with Styrene

The thermal stability of thermosets of DMESS-0.8 and DMESS-0.9 initiated by Luperox-P and Luperox 10M75 were measured at varying percentages of styrene and varying curing conditions. The results are shown in Table 9.

TABLE 9

Thermal stability of thermosets. $T_{5\%}$

| Resin (A:B) |  | DMESS-0.8 (1:9) | | | | DMESS-0.9 (1:9) | | | |
|---|---|---|---|---|---|---|---|---|---|
| Styrene (%) |  | 0 | 10 | 20 | 30 | 0 | 10 | 20 | 30 |
| Curing conditions | 150° C.-1 h, 175° C.-1 h, 200° C.-5 h | 331 | 327 | 331 | 333 | 316 | 306 | 324 | 321 |
|  | 150° C.-1 h, 175° C.-1 h, 200° C.-4 h | 336 | 330 | 337 | 331 | 342 | 318 | 332 | 318 |
|  | 150° C.-1 h, 175° C.-1 h, 200° C.-3 h | 335 | 341 | 335 | 334 | 330 | 334 | 332 | 336 |
|  | 150° C.-1 h, 175° C.-1 h, 200° C.-2 h | 335 | 318 | 334 | 322 | 333 | 327 | 326 | 237 |
|  | 150° C.-1 h, 175° C.-1 h, 200° C.-1 h | 328 | 334 | 318 | 302 | 333 | 320 | 317 | 323 |
|  | 150° C.-1 h, 175° C.-1 h | 325 | 330 | 323 | 331 | 337 | 329 | 322 | 324 |
|  | 120° C.-2 h | 313 | 312 | 309 | 304 |  |  |  |  |
|  | 120° C.-1 h | 329 | 328 | 329 | 319 |  |  |  |  |
|  | 120° C.-0.5 h | 311 | 311 | 313 | 287 |  |  |  |  |
|  | 90° C.-1.5 h | 326 | 316 | 313 | 304 |  |  |  |  |
|  | 90° C.-1 h | 309 | 307 | 298 | 299 |  |  |  |  |
|  | 120° C.-1 h, 150° C.-3 h | 322 | 316 | 306 | 311 |  |  |  |  |
|  | 90° C.-1 h, 120° C.-1 h, 150° C.-3 h | 315 | 312 | 325 | 311 |  |  |  |  |
|  | 70° C.-1 h, 90° C.-1 h, 120° C.-1 h | 300 | 305 | 303 | 296 |  |  |  |  |
|  | 70° C.-1 h, 90° C.-1 h, 150° C.-2 h | 332 | 325 | 312 | 311 |  |  |  |  |

Example 4.4—% Gel Content with Styrene

The % gel content of thermosets of DMESS-0.8 initiated by Luperox-P and Luperox 10M75 were measured for formulations containing varying percentages of styrene. The results are shown in Table 10.

TABLE 10

% Gel content of thermosets.
% Gel content

| | | DMESS-0.8 (1:9) | | | |
|---|---|---|---|---|---|
| Styrene (%) | | 0 | 10 | 20 | 30 |
| Curing conditions | 150° C.-1 h, 175° C.-1 h, 200° C.-5 h | 99.36 | 99.48 | 99.50 | 99.87 |
|  | 150° C.-1 h, 175° C.-1 h, 200° C.-2 h | 99.35 | 99.48 | 99.66 | 99.86 |
|  | 120° C.-2 h | 96.48 | 97.27 | 97.78 | 99.83 |
|  | 120° C.-1 h | — | 98.03 | 97.94 | 98.61 |
|  | 120° C.-0.5 h | 95.44 | 97.01 | 97.58 | 98.36 |
|  | 90° C.-1.5 h | 95.37 | 96.03 | 95.90 | 97.00 |
|  | 90° C.-1 h | 88.94 | 93.52 | 96.95 | 97.63 |
|  | 120° C.-1 h, 150° C.-3 h | 98.99 | 99.41 | 99.91 | 99.67 |
|  | 90° C.-1 h, 120° C.-1 h, 150° C.-3 h | 98.79 | 99.74 | 99.69 | 99.59 |
|  | 70° C.-1 h, 90° C.-1 h, 120° C.-1 h | 97.69 | 97.34 | 97.94 | 99.15 |

Example 5—Methacrylate-Acetate Epoxidized Sucrose Soyate (MAcetSS) Oligomers A reaction kettle was charged with epoxidized sucrose soyate (ESS), hydroquinone, ATC-3, and methacrylic acid (A). The reaction was mechanically stirred at 100° C. Once the acid number goes down, the methacrylic anhydride (B) and acetic anhydride (C) mixture was then added dropwise. See Reaction 3 where the epoxidized sucrose soyate with its epoxide groups is represented by the $R_1$, $R_2$ oxirane structure. The reaction progress was monitored by performing titrations to determine the acid number. Two resins were synthesized: MAcetSS-0.1 and MAcetSS-0.3. The numbers indicate the ratio of acetic anhydride to 1 part methacrylic anhydride. Table 11 shows the summary of the properties of all three resins.

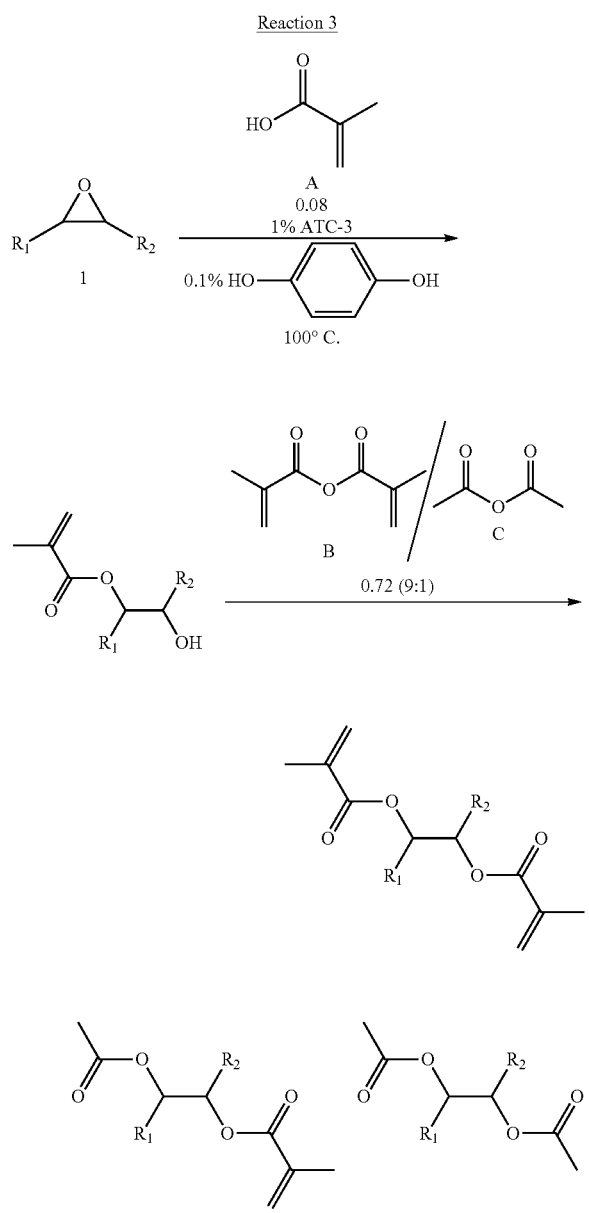

Reaction 3

TABLE 11

Properties of the resins.

| Resin | Time (Hours) | Acid Number | % Solids | Viscosity (Pa · s) | $M_n$ | Đ |
|---|---|---|---|---|---|---|
| DMESS-0.8 (1:9) | 47.5 | 7 | 99.90 | 67.3 | 3905 | 1.012 |
| MAcetSS-0.1 | 25 | 4 | 99.09 | 46.5 | 3754 | 1.011 |
| MAcetSS-0.3 | 24 | 8 | 98.08 | 24.1 | 3631 | 1.012 |

Figure 8:
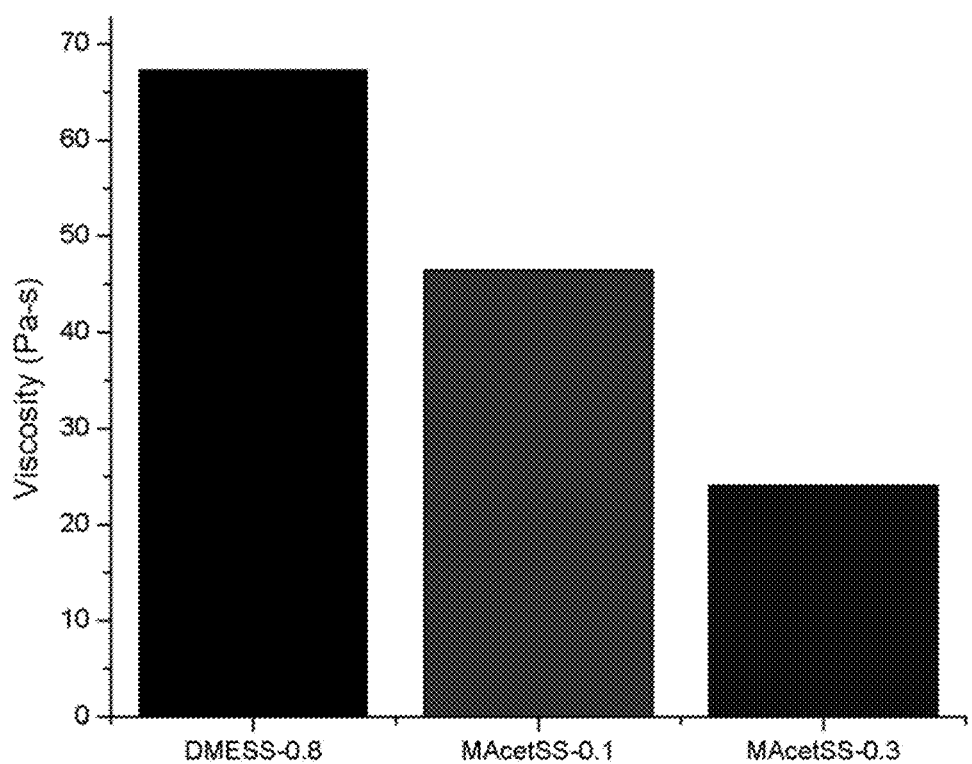
FIG. 8 shows the viscosity of the DMESS-0.8 (1:9) and MAcetSS resins in Example 5.
Figure 9:
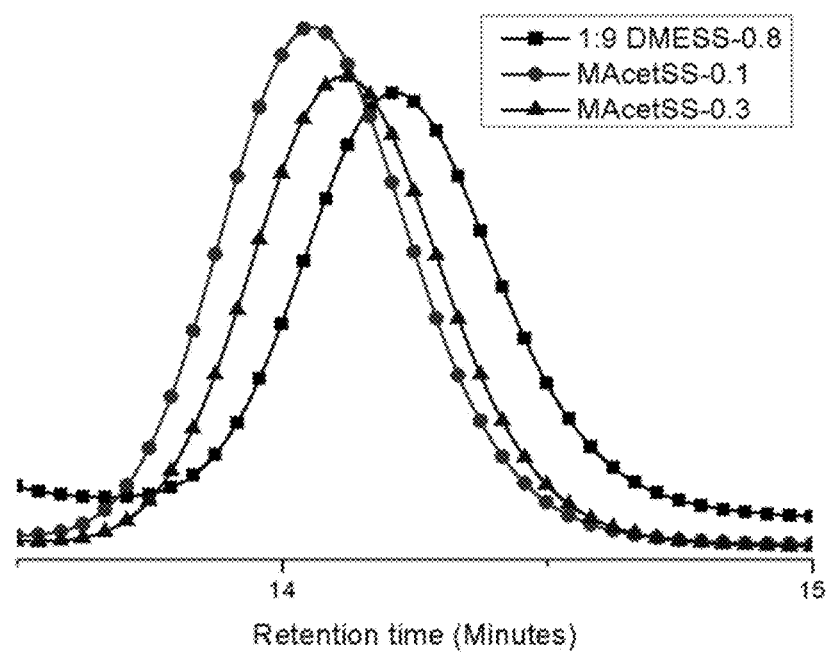
FIG. 9 shows the GPC traces for the DMESS-0.8 (1:9) and MAcetSS resins in Example 5.

The synthesis of the resins showed that MAcetSS synthesis was twice as fast as the DMESS-0.8 (1:9) synthesis. This could suggest that the reactions involving the acetate are much faster than the methacrylates. In all cases, the acid numbers were less than 10 and the % solids were all greater than 98%. FIG. 8 shows the viscosity trend. The incorporation of the acetate groups proved to lower the viscosity of the resin. The number-average molecular weight ($M_n$) gradually decreased as the amount of acetates was increased. This is expected since smaller acetate groups were replacing the heavier methacrylates. FIG. 9 shows the GPC trace of the resins.

Figure 10:
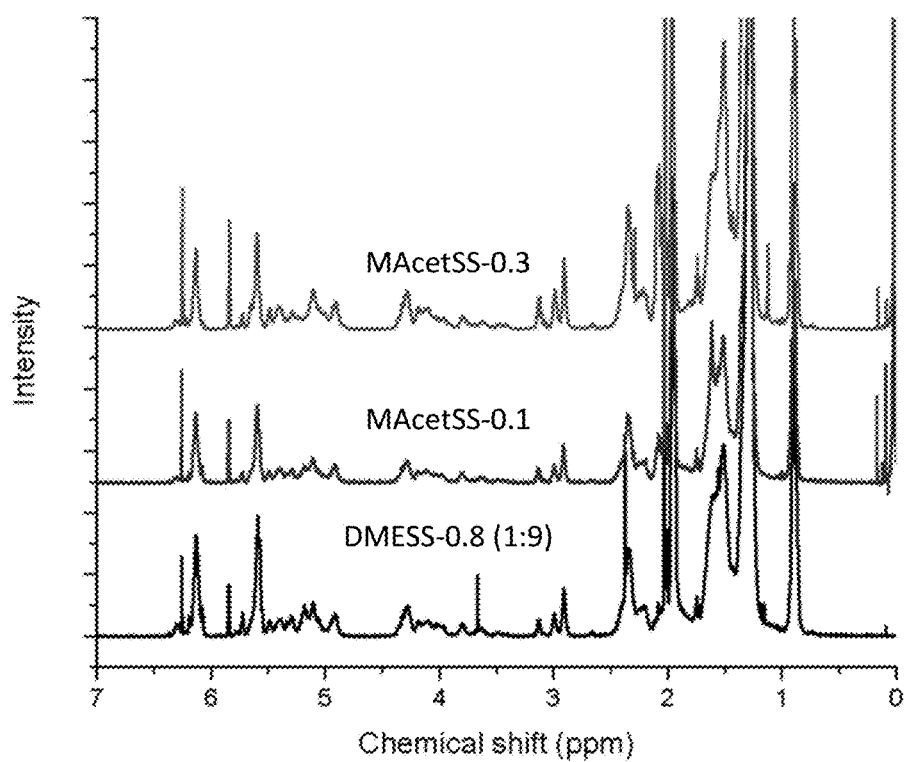
FIG. 10 depicts the proton NMR spectra of the DMESS-0.8 (1:9) and MAcetSS resins in Example 5.

The proton NMR spectra (FIG. 10) of the DMESS-0.8 (1:9) and MAcetSS resins were very similar with each other. The main difference can be observed at the chemical shift around 5.2 ppm. This peak corresponds to the proton of the —CH— of the second methacrylate group of DMESS-0.8 (1:9). The spectra shows lowering of this peak as the amount of acetate groups was increased.

Figure 11A:
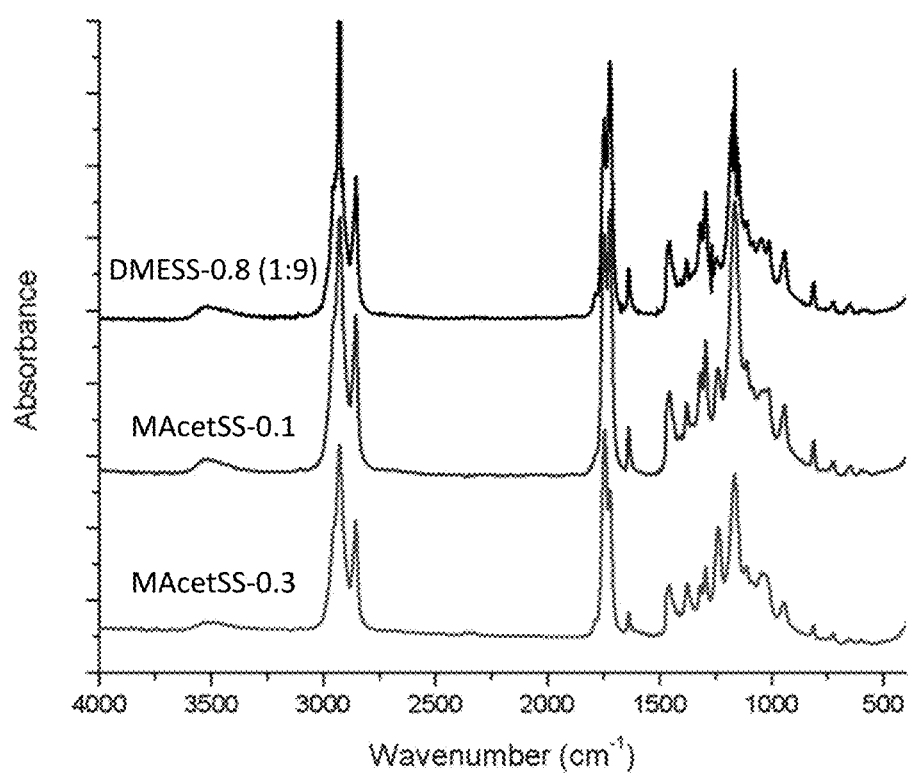
FIGS. 11a and 11b depict the FTIR spectra of the DMESS-0.8 (1:9) and MAcetSS resins in Example 5, full spectrum (FIG. 11a) and carbonyl region (FIG. 11b).
Figure 11B:
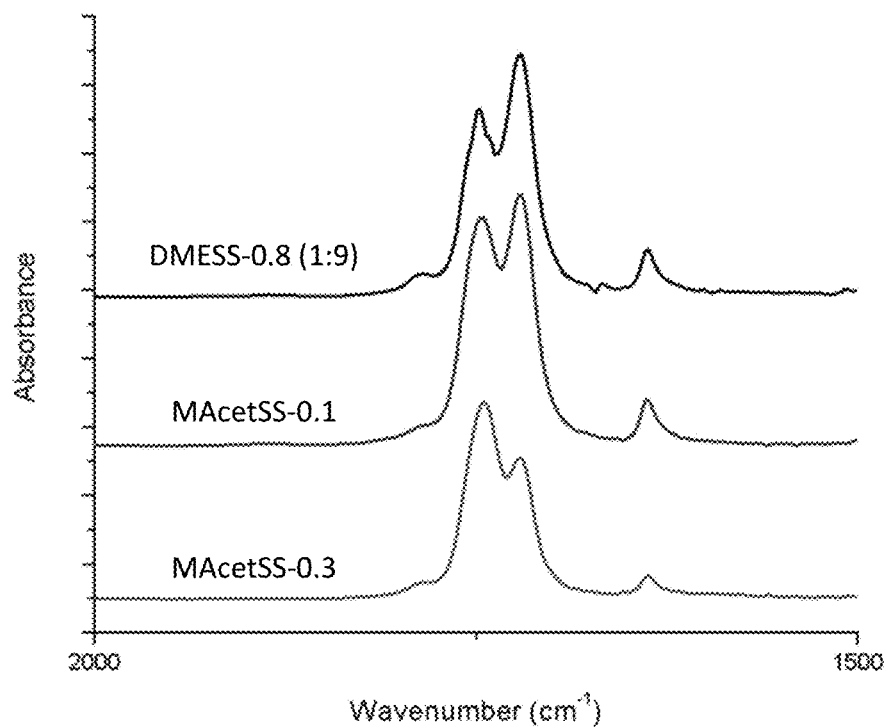

The FTIR spectra (FIG. 11) of the MAcetSS resins showed all the functional groups present in comparison to DMESS-0.8 (1:9). FIG. 11a shows the full FTIR spectrum. The carbonyl peaks (FIG. 11b) showed that the aliphatic carbonyl peaks increased as more acetate groups replaced the methacrylates.

Example 5.1—Viscosities with Styrene

Figure 12:
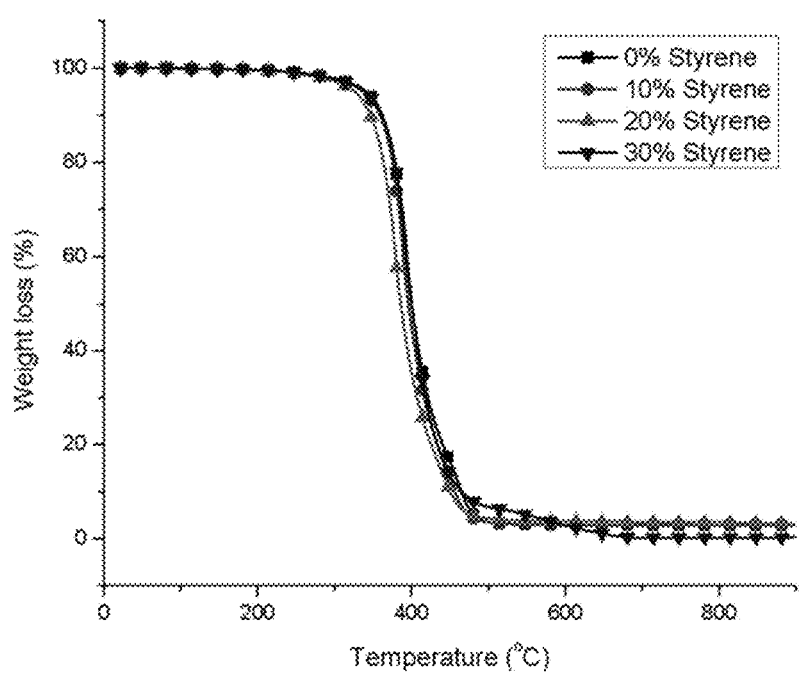
FIG. 12 shows the TGA curve of MAcetSS-0.1-based thermosets containing 0, 10, 20, and 30% styrene.

In this example, the same formulations and initiators were utilized for the MAcetSS as described for DMESS-0.8 (1:9) in Example 4.3, above. The formulations were all cured in the oven at 70° C. for 1 hour, 90° C. for 1 hour, and 150° C. for 2 hours. The thermal stability of the thermosets was characterized via thermogravimetric analysis (TGA), the temperatures of 5% weight loss and % gel are listed on Table 12. 5% weight loss was observed at temperatures greater than 311° C. for all the thermosets. There was a slight improvement in the thermal stability of the MAcetSS-based thermosets compared with the DMESS-0.8 (1:9)-based thermosets. The % gel content of all the thermosets were over 98.11%. FIG. 12 shows the TGA curve of MAcetSS-0.1-based thermosets containing 0, 10, 20, and 30% styrene. The same type of curve was observed with the MAcetSS-0.3-based thermosets.

TABLE 12

Thermal properties and % gel content of thermosets.

| | $T_{5\%}$ (° C.) | | | % Gel content | | |
|---|---|---|---|---|---|---|
| Styrene (%) | DMESS-0.8 (1:9) | MAcetSS-0.1 | MAcetSS-0.3 | DMESS-0.8 (1:9) | MAcetSS-0.1 | MAcetSS-0.3 |
| 0 | 332 | 341 | 339 | 98.80 | 98.60 | 98.11 |
| 10 | 325 | 338 | 334 | 98.68 | 98.72 | 98.22 |
| 20 | 312 | 325 | 328 | 98.55 | 98.87 | 98.81 |
| 30 | 311 | 340 | 323 | 98.70 | 99.05 | 99.40 |

Figure 13A:
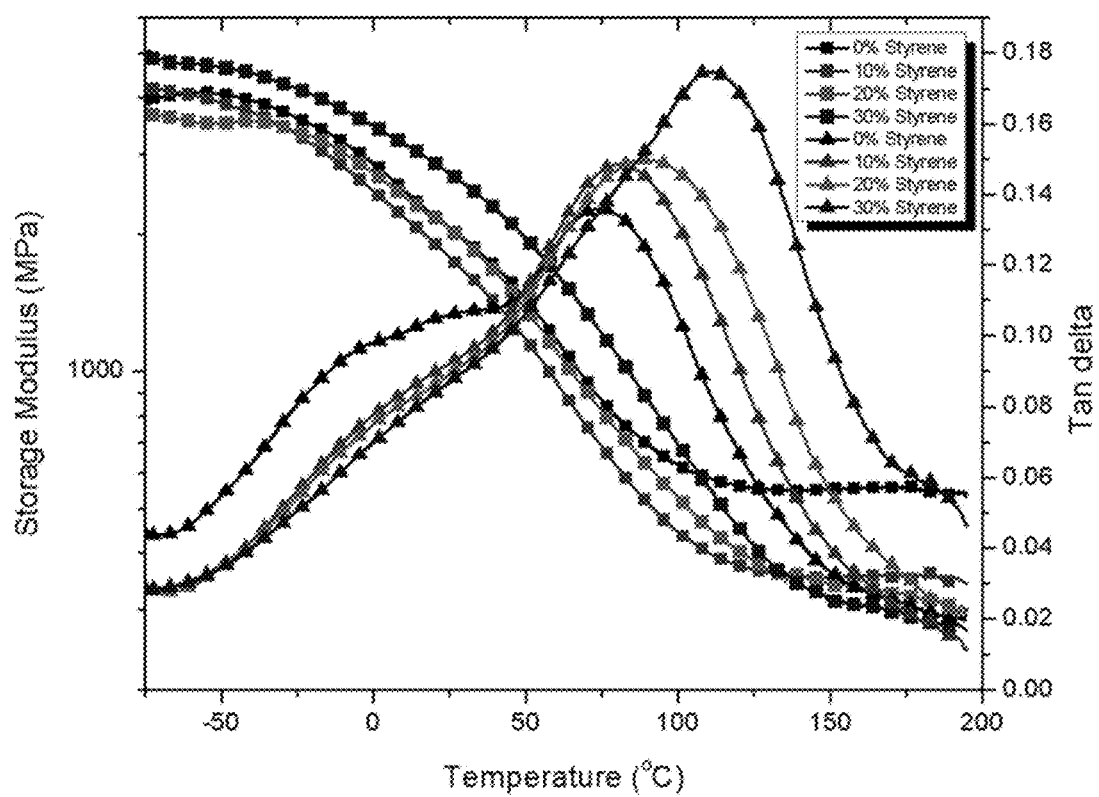
FIGS. 13a-c depict the DMTA curves of thermosets.
Figure 13B:
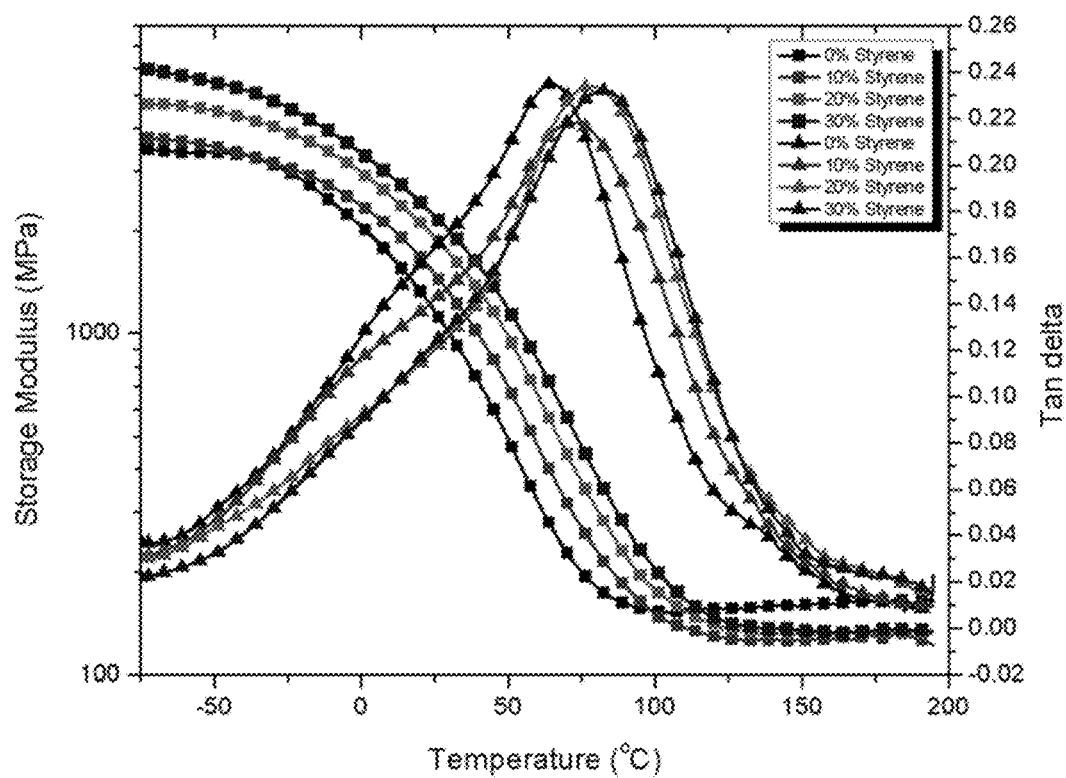
Figure 13C:
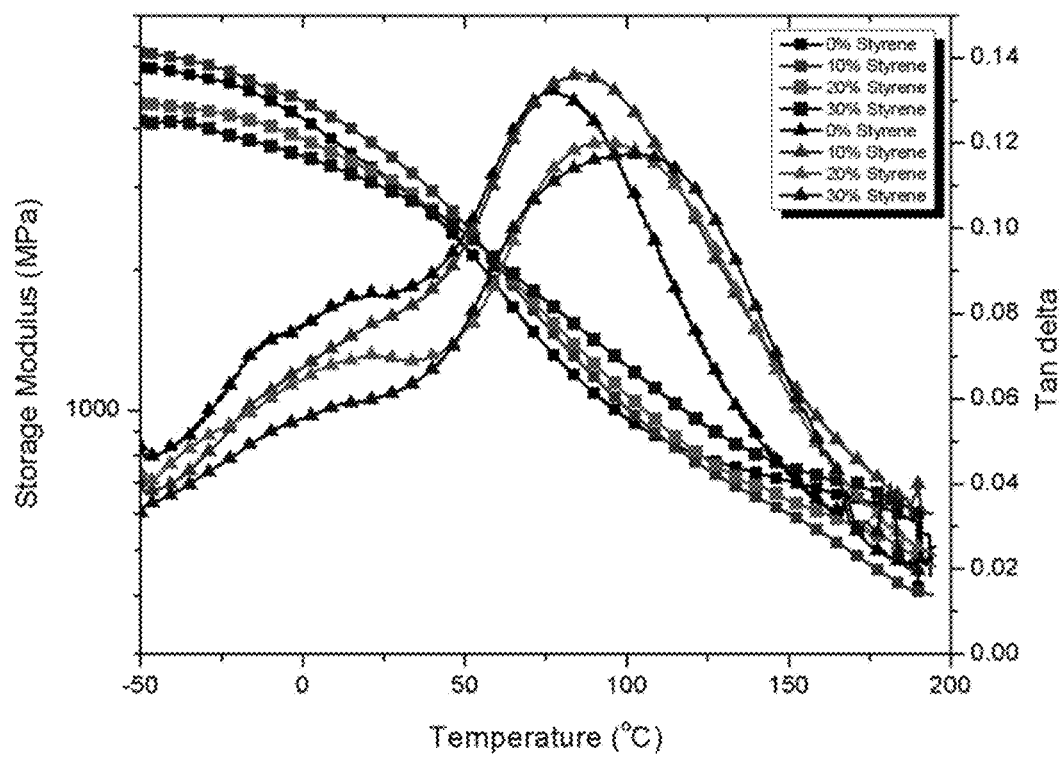
Figure 14:
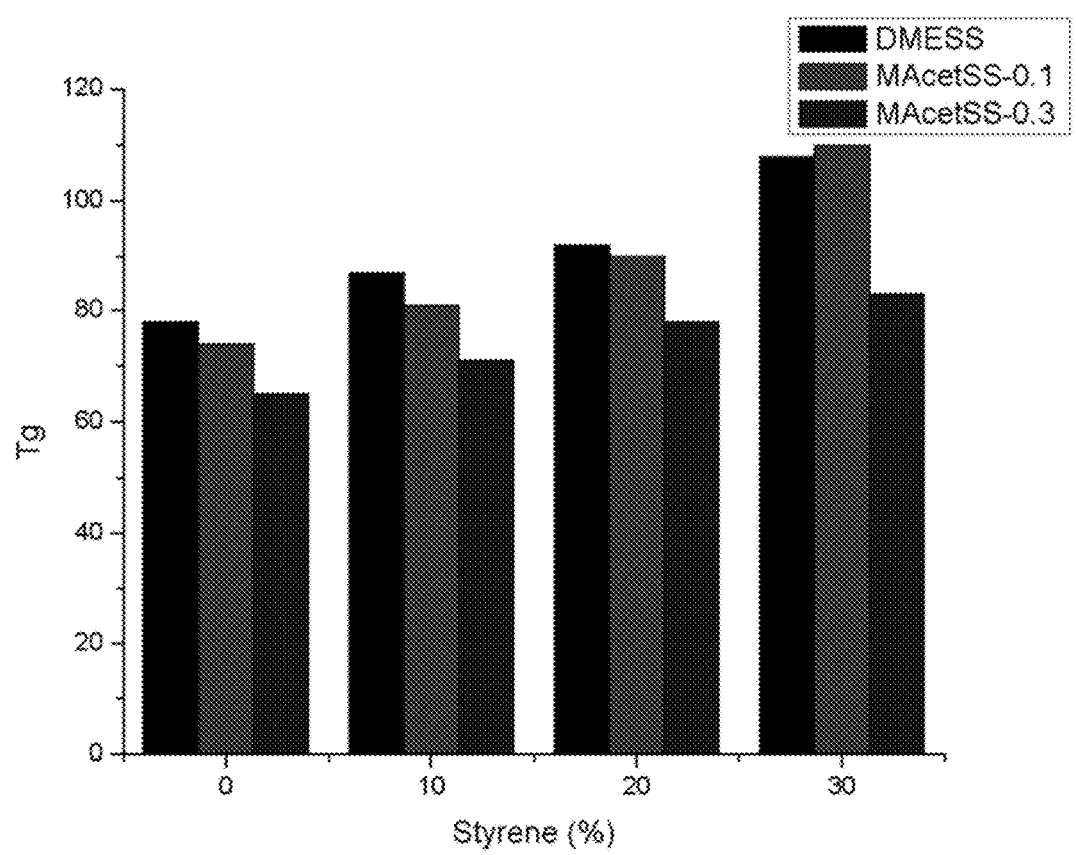
FIG. 14 depicts the $T_g$ of the DMESS-0.8 (1:9) and MAcetSS resins of Example 5 as functions of styrene content.
Figure 15:
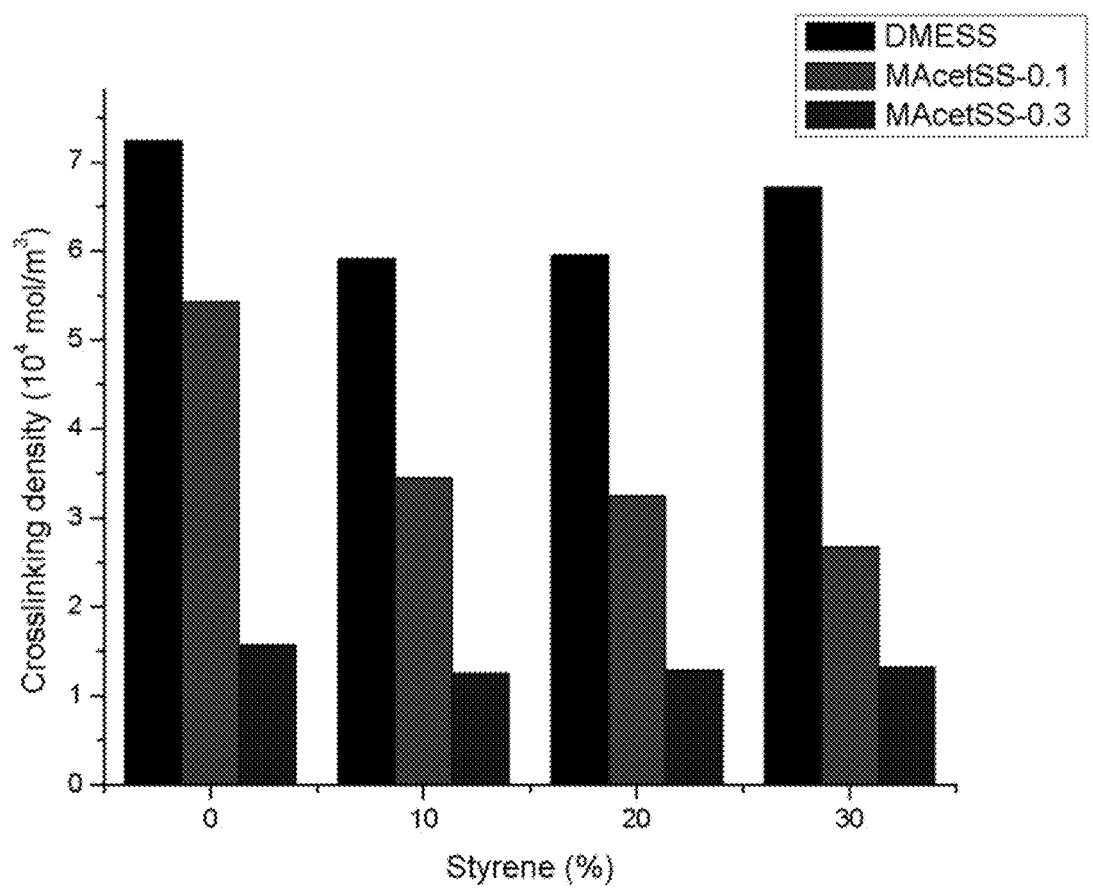
FIG. 15 depicts the crosslinking density, $v_e$, of the DMESS-0.8 (1:9) and MAcetSS resins of Example 5 as functions of styrene content.

The glass transition temperature ($T_g$) and crosslink density ($v_e$) were characterized via dynamic mechanical thermal analysis (DMTA), and the results are summarized in Table 13. FIGS. 13a-c depict the DMTA curves of thermosets: a) DMESS-0.8 (1:9), b) MAcetSS-0.1, and c) MAcetSS-0.3. The $T_g$ trend (FIG. 14) seems to be directly proportional to the styrene content and amount of methacrylates. $T_g$ increases as styrene content increases and decreases as more acetates replace the methacrylates. The crosslinking density, $v_e$, also follows the same trend (FIG. 15). The temperature dependence of storage modulus and tan δ for the thermosets with varying styrene content is illustrated in FIG. 13.

TABLE 13

Glass transition temperatures ($T_g$), storage moduli (E') at $T_g$ + 60° C., and crosslink densities ($v_e$) of thermosets.

| | $T_g$ (° C.) | | | E' (MPa) at $T_g$ + 60° C. | | | $v_e$ ($10^4$ mol/m³) | | |
|---|---|---|---|---|---|---|---|---|---|
| Styrene (%) | DMESS-0.8 (1:9) | MAcetSS-0.1 | MAcetSS-0.3 | DMESS-0.3 (1:9) | MAcetSS-0.1 | MAcetSS-0.3 | DMESS-0.8 (1:9) | MAcetSS-0.1 | MAcetSS-0.3 |
| 0 | 78 | 74 | 65 | 741.8 | 549.6 | 155.9 | 7.24 | 5.42 | 1.57 |
| 10 | 87 | 81 | 71 | 619.1 | 356.4 | 126.1 | 5.91 | 3.45 | 1.25 |
| 20 | 92 | 90 | 78 | 632.1 | 342.1 | 132.0 | 5.96 | 3.25 | 1.29 |
| 30 | 108 | 110 | 83 | 707.0 | 295.8 | 136.6 | 6.72 | 2.67 | 1.32 |

Figure 16A:
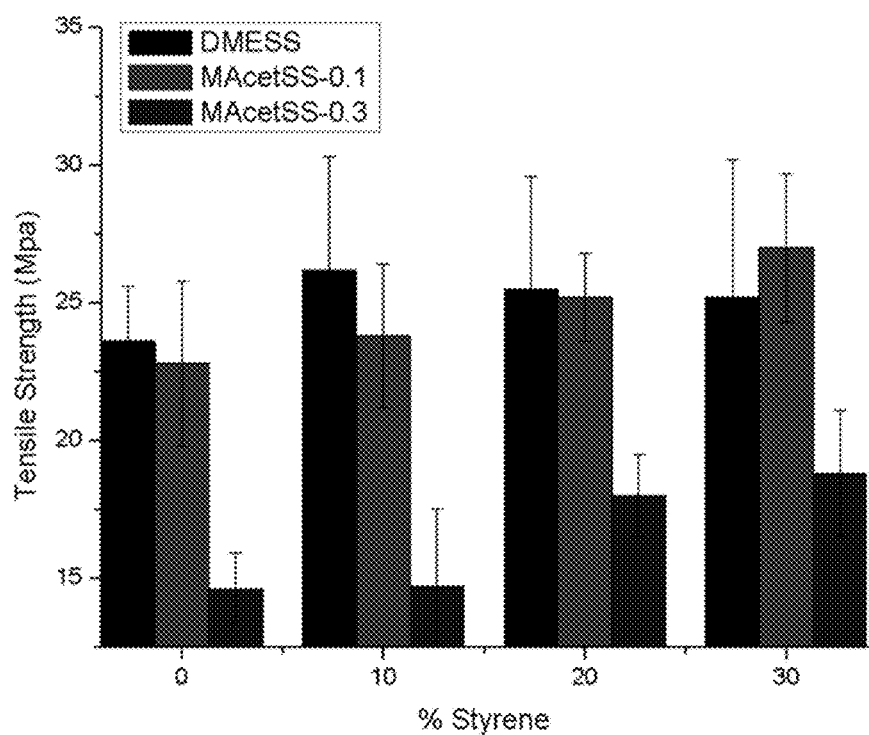
FIGS. 16a-d show the tensile properties for the DMESS-0.8 (1:9) and MAcetSS thermosets of Example 5 as a function of styrene content.
Figure 16B:
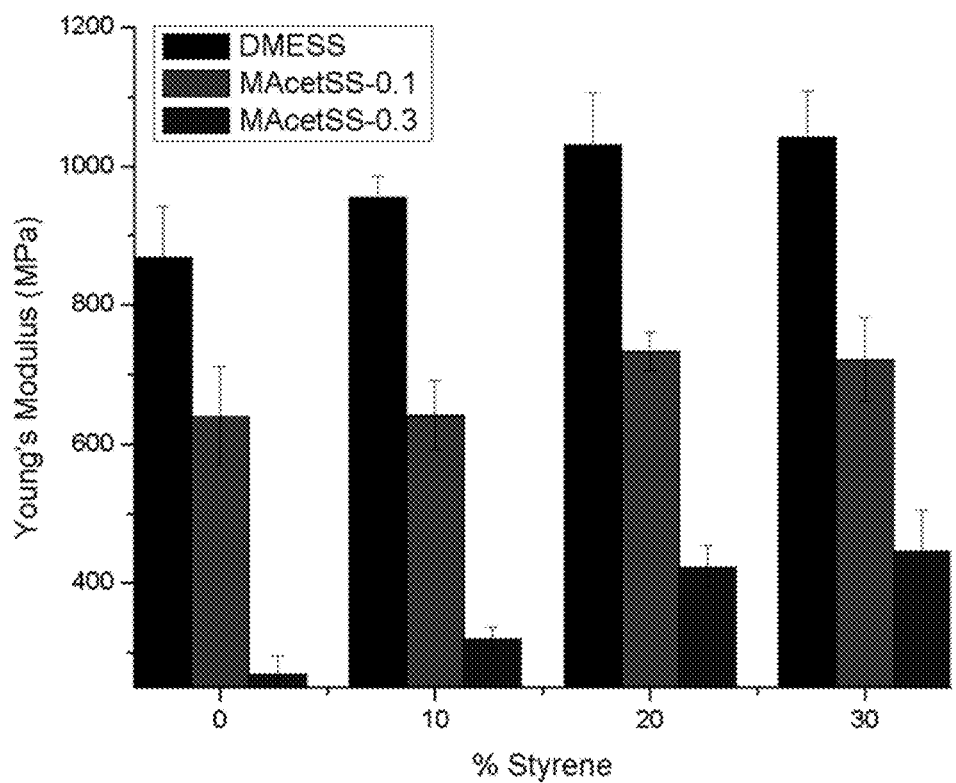
Figure 16C:
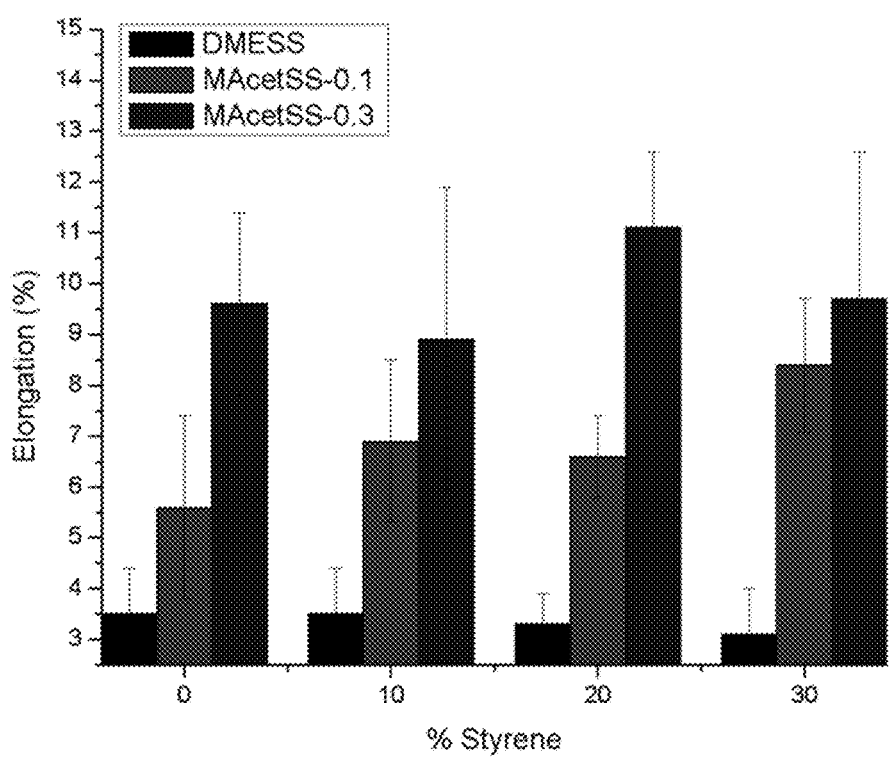
Figure 16D:
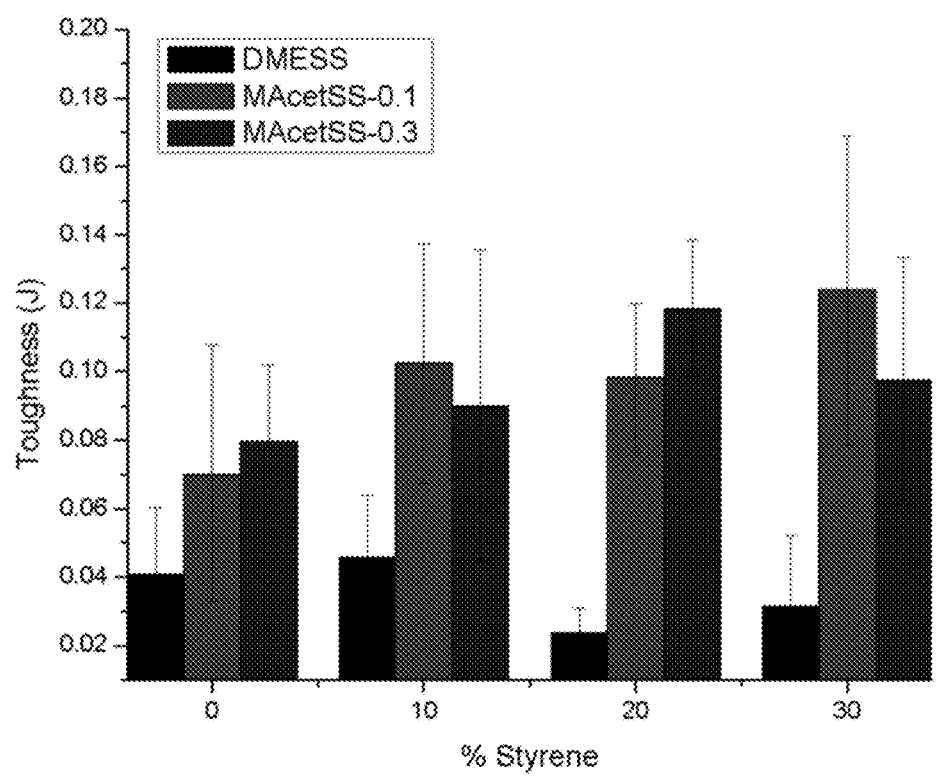

The tensile properties of the thermosets are summarized in Table 14. The trend (FIG. 16) seems to show that tensile strength, Young's modulus, % elongation, and toughness are directly proportional to the styrene content. In terms of decreasing amount of methacrylates (increasing amount of acetates), tensile strength (FIG. 16a) and Young's modulus (FIG. 16b) both decreased while % elongation (FIG. 16c) and toughness (FIG. 16d) increased.

TABLE 14

Tensile properties of thermosets.

| Resin | Styrene (%) | Tensile Strength (MPa) | Young's Modulus (MPa) | Elongation (%) | Toughness ($10^{-2}$ J) |
|---|---|---|---|---|---|
| DMESS-0.8 (1:9) | 10 | 26.2 ± 4.1 | 955 ± 32 | 3.5 ± 0.9 | 4.57 ± 0.02 |
| | 20 | 25.5 ± 4.1 | 1031 ± 75 | 3.3 ± 0.6 | 2.37 ± 0.01 |
| | 30 | 25.2 ± 5.0 | 1042 ± 66 | 3.1 ± 0.9 | 3.15 ± 0.02 |
| MAcetSS-0.1 | 10 | 23.8 ± 2.6 | 642 ± 50 | 6.9 ± 1.6 | 10.23 ± 0.03 |
| | 20 | 25.2 ± 1.6 | 734 ± 27 | 6.6 ± 0.8 | 9.83 ± 0.02 |
| | 30 | 27.0 ± 2.7 | 722 ± 60 | 8.4 ± 1.3 | 12.38 ± 0.05 |
| MAcetSS-0.3 | 10 | 14.7 ± 2.8 | 319 ± 17 | 8.9 ± 3.0 | 9.00 ± 0.05 |
| | 20 | 18.0 ± 1.5 | 422 ± 32 | 11.1 ± 1.5 | 11.83 ± 0.02 |
| | 30 | 18.8 ± 2.3 | 446 ± 60 | 9.7 ± 2.9 | 9.74 ± 0.04 |

The claimed invention is:

1. A polyfunctional bio-based oligomer which is the reaction product of:
   a) at least one epoxidized sucrose fatty acid ester resin;
   b) at least one ethylenically unsaturated acid selected from methacrylic acid, acrylic acid, crotonic acid, and mixtures thereof;
   c) at least one acid anhydride selected from acetic acid anhydride, acrylic acid anhydride, methacrylic acid anhydride, crotonic acid anhydride, and mixtures thereof;
   d) optionally, at least one catalyst; and
   e) optionally, at least one inhibitor;
wherein the ratio of ethylenically unsaturated acid to acid anhydride ranges from 90:1 to 1:90;
   at least one epoxide group of the at least one epoxidized sucrose fatty acid ester resin is esterified by at least one ethylenically unsaturated acid; and
   at least one epoxide group of the at least one epoxidized sucrose fatty acid ester resin is esterified by at least one acid anhydride.

2. The polyfunctional bio-based oligomer of claim 1, wherein the epoxidized sucrose fatty acid ester resin is epoxidized sucrose soyate.

3. The polyfunctional bio-based oligomer of claim 1, wherein the ethylenically unsaturated acid is methacrylic acid and the acid anhydride is selected from acetic acid anhydride, methacrylic acid anhydride, and mixtures thereof.

4. The polyfunctional bio-based oligomer of claim 1, wherein the epoxidized sucrose fatty acid ester resin is epoxidized sucrose soyate, the ethylenically unsaturated acid is methacrylic acid, and the acid anhydride is selected from acetic acid anhydride, methacrylic acid anhydride, and mixtures thereof.

5. The polyfunctional bio-based oligomer of claim 1, wherein the epoxide groups of the epoxidized sucrose fatty acid ester resin are substantially esterified by the ethylenically unsaturated acid and the acid anhydride.

6. The polyfunctional bio-based oligomer of claim 1, wherein a fraction of the epoxide groups of the epoxidized sucrose fatty acid ester resin is esterified by the ethylenically unsaturated acid and the acid anhydride.

7. A curable coating composition comprising:
   a) the polyfunctional bio-based oligomer of claim 1;
   b) optionally, at least one diluent;
   c) at least one initiator;
   d) optionally, at least one solvent; and
   e) optionally, at least one additive.

8. A curable coating composition of claim 7 wherein the epoxidized sucrose fatty acid ester resin is epoxidized sucrose soyate, the ethylenically unsaturated acid is methacrylic acid, and the acid anhydride is selected from acetic acid anhydride, methacrylic acid anhydride, and mixtures thereof.

9. A curable coating composition of claim 7 wherein the diluent is present in an amount ranging from 5 to 80 percent of the total weight of the curable coating composition.

10. A curable coating composition of claim 9 comprising styrene as a diluent.

11. A method of making a polyfunctional bio-based oligomer comprising the step of reacting:
   a) at least one epoxidized sucrose fatty acid ester resin;
   b) at least one ethylenically unsaturated acid selected from methacrylic acid, acrylic acid, crotonic acid, and mixtures thereof; and
   c) at least one acid anhydride selected from acetic acid anhydride, acrylic acid anhydride, methacrylic acid anhydride, crotonic acid anhydride, and mixtures thereof;
   optionally, in the presence of at least one catalyst and/or at least one inhibitor;
wherein the ratio of ethylenically unsaturated acid to acid anhydride ranges from 90:1 to 1:90.

12. A method of claim 11, wherein the epoxidized sucrose fatty acid ester resin is epoxidized sucrose soyate, the ethylenically unsaturated acid is methacrylic acid, and the acid anhydride is selected from acetic acid anhydride, methacrylic acid anhydride, and mixtures thereof.

13. A method claim 11, wherein the epoxidized sucrose fatty acid ester resin is first reacted with the ethylenically unsaturated acid to form a first esterified product followed by reacting the first esterified product with the acid anhydride.

14. A method claim 12, wherein the epoxidized sucrose fatty acid ester resin is first reacted with the ethylenically unsaturated acid to form a first esterified product followed by reacting the first esterified product with the acid anhydride.

* * * * *